United States Patent
Damar et al.

(10) Patent No.: US 10,548,629 B2
(45) Date of Patent: Feb. 4, 2020

(54) DEVICE AND METHOD FOR FOLLICULAR UNIT TRANSPLANTATION

(71) Applicants: Olcay Yilmaz Damar, Istanbul (TR); Kadir Oz, Istanbul (TR)

(72) Inventors: Olcay Yilmaz Damar, Istanbul (TR); Kadir Oz, Istanbul (TR)

(73) Assignee: Olcay Yilmaz Damar, Istanbul (TR)

( * ) Notice: Subject to any disclaimer, the term of this patent is extended or adjusted under 35 U.S.C. 154(b) by 327 days.

(21) Appl. No.: 15/313,107

(22) PCT Filed: May 20, 2015

(86) PCT No.: PCT/EP2015/061076
§ 371 (c)(1),
(2) Date: Nov. 22, 2016

(87) PCT Pub. No.: WO2015/177191
PCT Pub. Date: Nov. 26, 2015

(65) Prior Publication Data
US 2017/0181766 A1 Jun. 29, 2017

(30) Foreign Application Priority Data
May 23, 2014 (EP) .................................... 14169570

(51) Int. Cl.
| A61B 17/34 | (2006.01) |
| A61B 17/3205 | (2006.01) |
| A61B 90/11 | (2016.01) |
| A61B 17/00 | (2006.01) |
| A61B 17/32 | (2006.01) |

(52) U.S. Cl.
CPC .... *A61B 17/3403* (2013.01); *A61B 17/32053* (2013.01); *A61B 17/3468* (2013.01); *A61B 90/11* (2016.02); *A61B 2017/00022* (2013.01); *A61B 2017/00752* (2013.01); *A61B 2017/00969* (2013.01); *A61B 2017/320064* (2013.01); *A61B 2017/3405* (2013.01)

(58) Field of Classification Search
CPC ............ A61B 17/3403; A61B 17/3468; A61B 17/32053; A61B 90/11; A61B 90/14; A61B 2017/00969; A61B 2017/00752; A61B 2017/00022; A61B 2017/320064; A61B 2017/3405; A61B 2017/3407; A61B 2017/3409
See application file for complete search history.

(56) References Cited

U.S. PATENT DOCUMENTS

| 5,989,279 | A | 11/1999 | Rassman |
| 7,621,933 | B2 * | 11/2009 | Bodduluri ........ A61B 17/32053 606/187 |
| 2001/0034534 | A1 | 10/2001 | Transue |

(Continued)

*Primary Examiner* — Erich G Herbermann
(74) *Attorney, Agent, or Firm* — Gokalp Bayramoglu

(57) ABSTRACT

Present invention relates to a transplantation device for transplanting a follicular unit which comprises a gripper, a rail mechanism, a gripper holding mechanism, at least one camera and/or sensor and a plurality of motors. Also a gripper for harvesting and implanting a follicular unit including a cutting mechanism, a knife mechanism, a tubular body and an ejector is disclosed. Furthermore, independent claims are included for covering a method for follicular unit transplantation and a method for harvesting and implanting of a follicular unit.

11 Claims, 18 Drawing Sheets

(56) References Cited

U.S. PATENT DOCUMENTS

2007/0106306 A1    5/2007   Bodduluri et al.
2009/0087830 A1*   4/2009   Oostman ............... A61B 17/00
                                                         435/4
2013/0010081 A1    1/2013   Tenney et al.

* cited by examiner

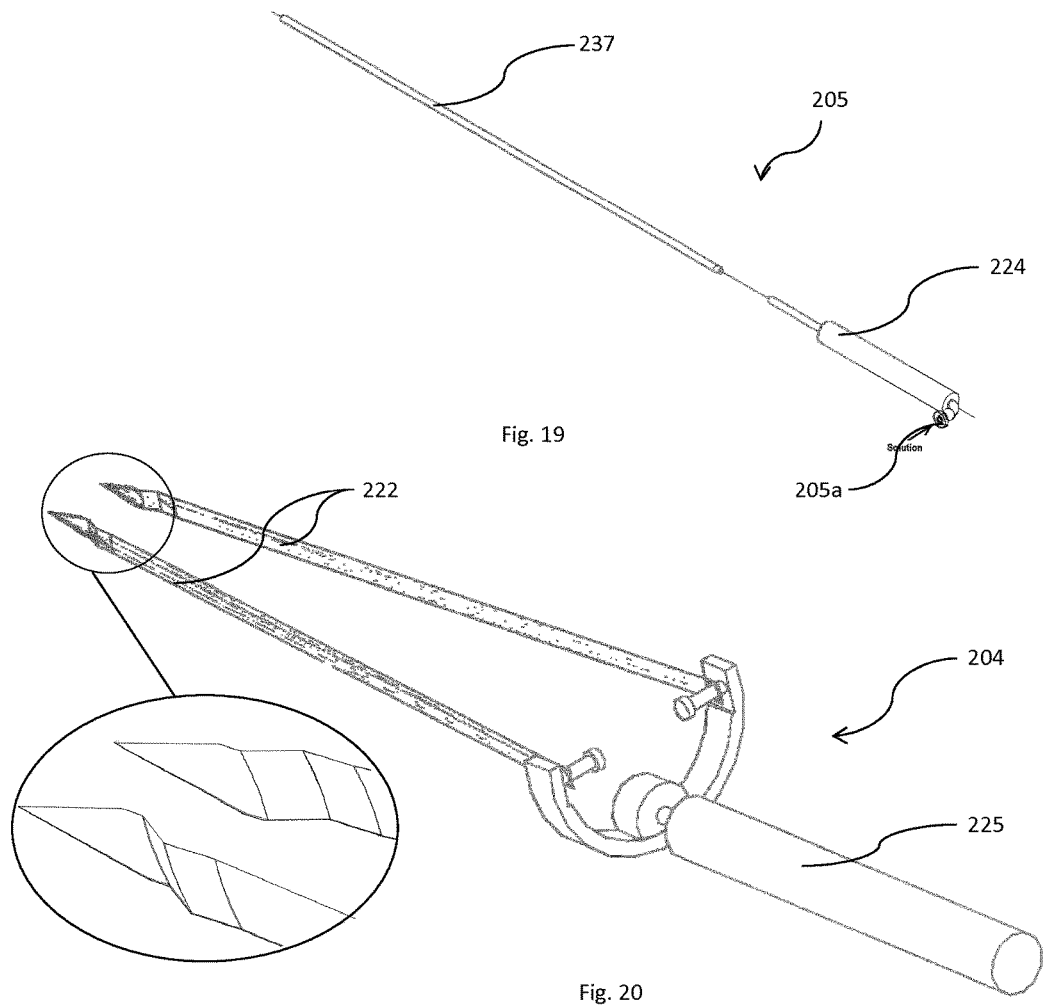
Fig. 19
Fig. 20
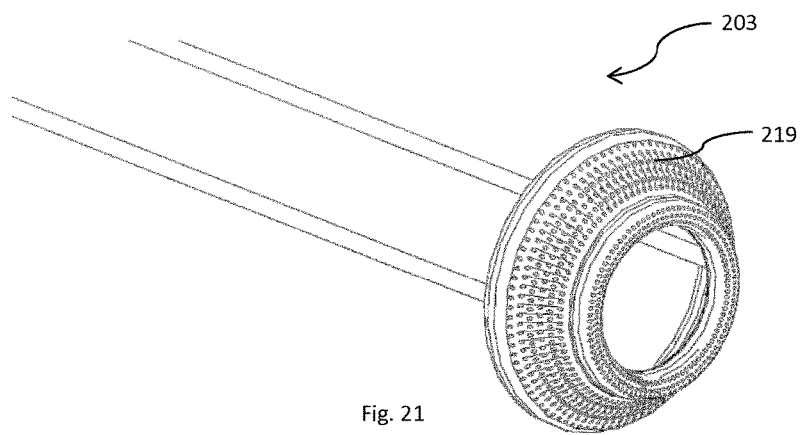
Fig. 21

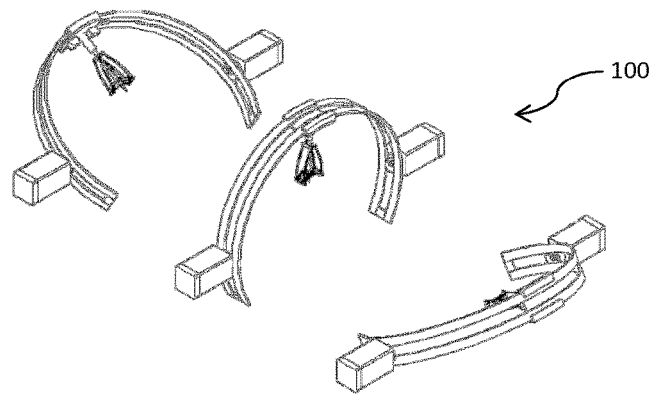
Fig. 42a
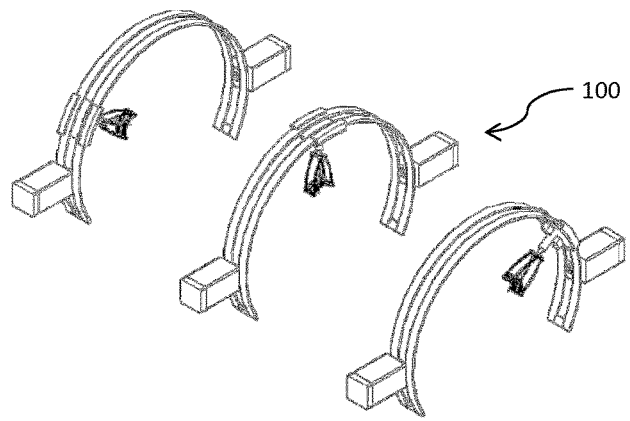
Fig. 42b
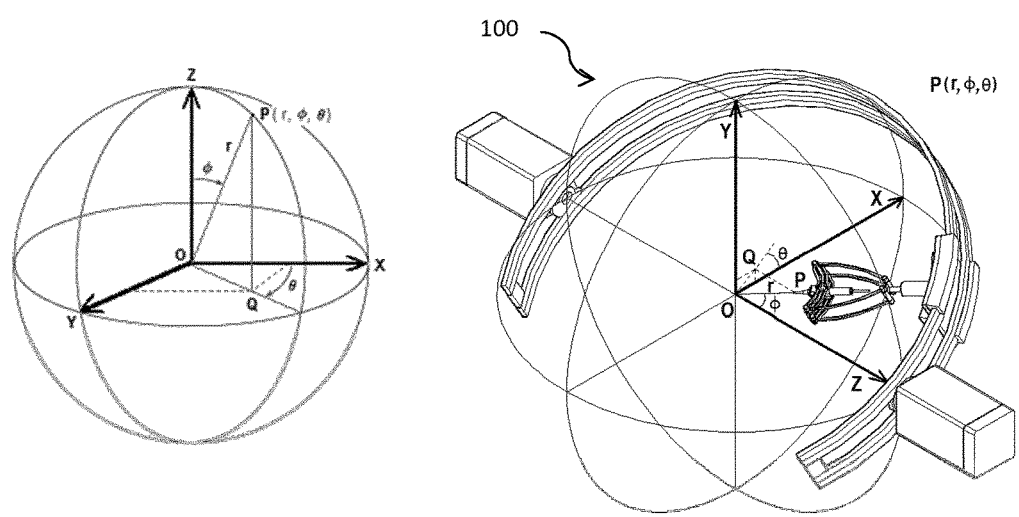
Fig. 43a
Fig. 43b

DEVICE AND METHOD FOR FOLLICULAR UNIT TRANSPLANTATION

CROSS REFERENCE TO RELATED APPLICATIONS

This application is a national phase application of International Application No. PCT/EP2015/061076, filed on May 20, 2015, which is based upon and claims priority to European Patent Application No. 14169570.0 filed on May 23, 2014, the entire contents of which are incorporated herein by reference.

TECHNICAL FIELD OF THE INVENTION

The present invention relates to a device which is able to be used for all known steps of follicular unit transplantation device and a method accordingly. In a more specific manner, the present invention provides a follicular unit transplantation device which is specifically designed to perform harvesting and implantation phases of the transplantation operation in a very short time and with a maximum efficiency.

BACKGROUND OF THE INVENTION

In the field of transplantation, especially in hair transplantation, FUT & FUE techniques, methods of obtaining follicular unit manually, are well known and applied for many years. In these methods, all phases of the operation, especially harvesting and implanting steps, are performed by an operator. Follicular unit transplantation (FUT) is a hair restoration technique where patient's hair is transplanted in naturally occurring groups of 1 to 4 hairs. Hairs follicular units are taken collectively by the expert team then separated. One problem with associated is that follicular unit transplantation (FUT) is an invasive technique and leaves a linear scar in the donor area. Although the scar fades with time, it could still be a bit visible.

In FUE harvesting, individual follicular units are extracted directly from the hair restoration patient's donor area, generally one by one. Extracted grafts are separated into groups according to their follicular numbers. During, the separation of the collected follicular units, the follicular unit harvesting phase is completed and then as a preparation for the implantation phase; the opening process of the incisions, is started on the recipient site. The process of the incisions on the body surface is achieved according to the determined area for the implantation. After the completion of the slits/incisions opening process: the implantation process is started. The implantation process is achieved by implanting the grafts into the opened slits on the recipient site which is a bald area. One of the major disadvantages of FUE technique is that it is time consuming, and a limited number of follicular units can be harvested to the donor area per session. The average amount of grafts extracted in a single day may vary from 1000 to 3000 depending on follicular unit type and skin conditions and hair loss type of the patient. If more graft/follicular unit are needed, more than one session is suggested. This is a very time-consuming situation for the patient.

Moreover, in these kinds of applications, several situations affect negatively the efficiency of the follicular unit transplantation operation. A problem associated with these kinds of techniques, during the follicular unit implantation operation, the follicular units are touched several times and every touch damages the follicular units. In addition, if transplantation session period extends, the efficiency of the follicular unit transplantation decreases. The adaptation performance of the newly implanted follicular unit decreases. Surgeons mostly use a handheld tool that punches each follicular unit in the donor area. These techniques are more difficult and time consuming, especially in many countries, where the cost of highly experienced staff labor is much expensive.

Recently, robotic systems for the follicular unit transplantation are proposed. A prior art reference, among many others, relevant to the technical field of the present invention is the U.S. Pat. No. 7,621,933 (B2) publication. It discloses a multi-part tool assembly for harvesting and implanting follicular units, comprising an outer cannula having an open, tissue-piercing distal end, and an inner canmila coaxially positioned in a lumen of the first cannula, the second cannula having an open, tissue-coring distal end sized to engage and retain single hair follicular units. The document addressing multi-part tool assembly is however silent about to achieve all steps, of the hair transplantation operations automatically and consist of very complex mechanical parts.

Another prior art reference relevant to the technical field of the present invention is the US2007106306 (A1) publication. It discloses automated system for harvesting or implanting follicular units. An automated system for harvesting of implanting follicular units, including a moveable arm; a harvesting and/or implantation tool mounted on the moveable arm; one or more cameras mounted on the moveable arm; a processor configured to receive and process images acquired by the one or more cameras; and a controller operatively associated with the processor and configured to position the moveable arm based. The moveable arm is positionable such that the tool may be positioned at a desired orientation relative to an adjacent body surface. In these type of devices, tools are for harvesting and implanting are generally attached to a very complex and heavy robotic structures that cause to the decrease of the velocity and the accelerations of the system (of the harvesting/implanting tools). In addition that this tools perform at very low levels.

The present invention therefore provides a robot system for follicular unit transplantation overcoming the aforementioned inconveniences, which is as defined in Claim 1.

SUMMARY OF THE INVENTION

Primary object of the present invention is to provide a follicular unit transplantation device that removes the follicular unit from the donor area and places directly into the recipient site in a very short time with rapid healing and without disruption of normal routine life of the patient.

Another object of the present invention is to provide a follicular unit transplantation device that decreases the risks of operator error and mishandling of the follicular unit—all of which can lead to damage to the follicles and poor growth with undesired appearance.

Another Object of the present invention is to provide a follicular unit transplantation device that allows to transplant hundreds to thousands of individual follicular unit by obtaining homogeneity at the scalp of the patient comparing to the manual techniques without leaving a linear scar.

Another object of the present invention is to provide a follicular unit transplantation device that removes follicular units with less tension and torsion by preventing to lose of its liveliness.

Further, a follicular unit transplantation device uses spherical coordinate system which allows reaching every point of the whole scalp of the patient by using less parameter than complex systems with providing a lighter structure.

A transplantation device comprises a gripper for harvesting and implanting the follicular unit, a rail mechanism comprising at least one rail for positioning the gripper at a predetermined orientation with respect to a donor or a recipient area, a gripper holding mechanism for holding said gripper attached to said rail mechanism, at least one camera and/or sensor for image acquisition to identify and determine a relative position and orientation of said gripper, a plurality of motors for positioning of said gripper and said rail mechanism. Said gripper for harvesting and implanting a follicular unit, comprises a cutting mechanism formed of a plurality of blades for penetrating the outer periphery of a selected follicular unit on a donor area, a knife mechanism for opening an incision on a recipient area, a tubular body moves along the circumference of the cutting mechanism to hold tightly or loose said follicular unit, an ejector for pushing said follicular unit into the incision. A method for follicular unit transplantation, comprises, acquiring and processing images of a donor area of a body surface to select and determine a relative position and orientation of a follicular unit to be harvested, positioning a gripper by using a rail mechanism and a gripper holding mechanism, harvesting the selected follicular unit by movement of a cutting mechanism of the gripper that penetrates periphery of selected follicular unit, withdrawing the gripper with the selected follicular unit retained in the cutting mechanism of the gripper, acquiring and processing the images of a recipient site, repositioning the gripper holding mechanism by using the rail mechanism for implanting the follicular unit to the recipient area, using a knife mechanism of the gripper for opening an incision on the recipient area, implanting the follicular unit by movement of the gripper into the incision. A method for harvesting and implanting of a follicular unit, comprises, using a cutting mechanism for penetrating the outer periphery of a selected follicular unit on a donor area, moving a tubular body to hold tightly follicular unit which is already encapsulated by the cutting mechanism, withdrawing the gripper from the donor area with the follicular unit retained in the cutting mechanism, opening an incision on a recipient area by using a knife mechanism, moving the tubular body to loose follicular unit which is hold by the cutting mechanism, implanting the follicular unit into the incision by using an ejector, while the knife mechanism is withdrawn from the incision, the cutting mechanism is pushed to the incision, repositioning of cutting mechanism with at least one motor.

BRIEF DESCRIPTION OF THE DRAWINGS

Accompanying drawings are given solely for the purpose of exemplifying a follicular unit transplantation device whose advantages over prior art were outlined above and will be explained hereinafter in brief. The drawings are not meant to delimit the scope of protection as identified in the claims nor should they be referred to alone in an effort to interpret the scope identified in said claims without recourse to the technical disclosure in the description of the present invention.

FIG. 19 demonstrates a perspective view of an ejector of the transplantation device according to the present invention.

FIG. 20 demonstrates a perspective view of a knife mechanism of the tansplantation device according to the present invention.

FIG. 21 demonstrates a partial perspective view of a safety member of the transplantation device according to the present invention.

FIG. 42a demonstrates perspective views of a transplantation device where the displacement of the rail to which an alternated gripper holding mechanism attached according to the present invention.

FIG. 42b demonstrates perspective views of a transplantation device where the displacement of the gripper and rail to which an alternated gripper holding mechanism attached according to the present invention.

FIG. 43a demonstrates the perspective views of an illustration of the spherical coordinate system.

FIG. 43b demonstrates the perspective views of a transplantation device where the illustration of the spherical coordinate system is shown according to the present invention.

DETAILED DESCRIPTION OF THE INVENTION

Figure 1:
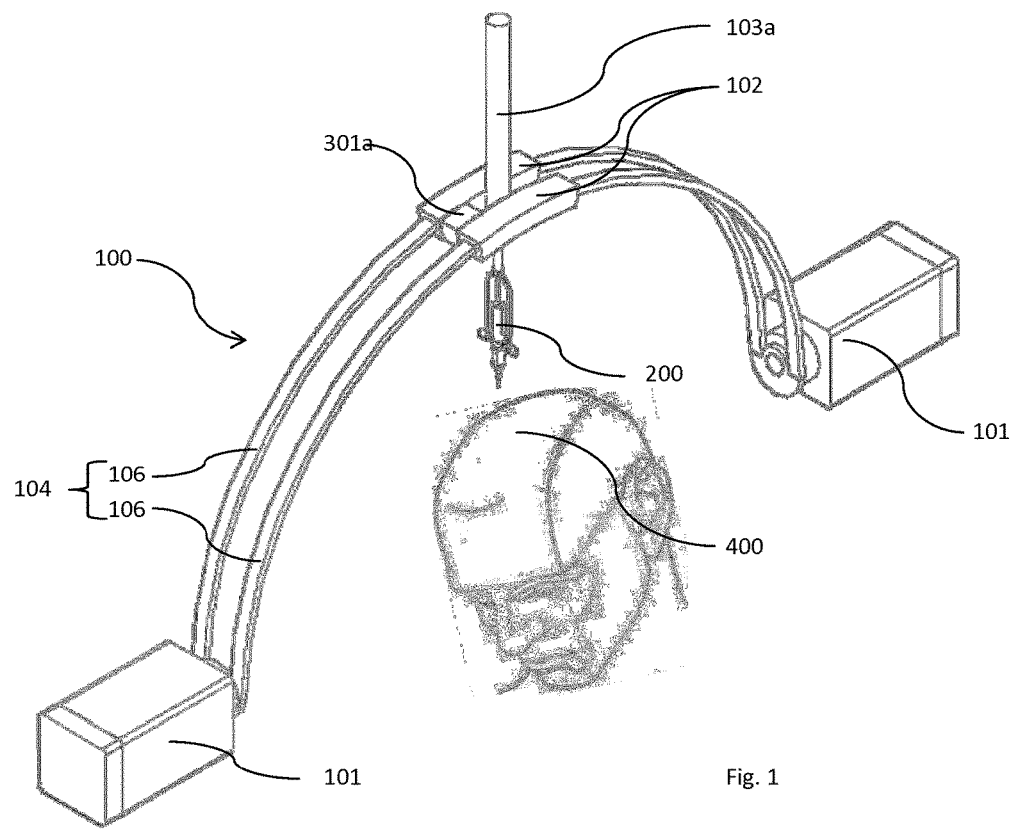
FIG. 1 demonstrates a perspective view of the transplantation device according to the present invention.
Figure 2:
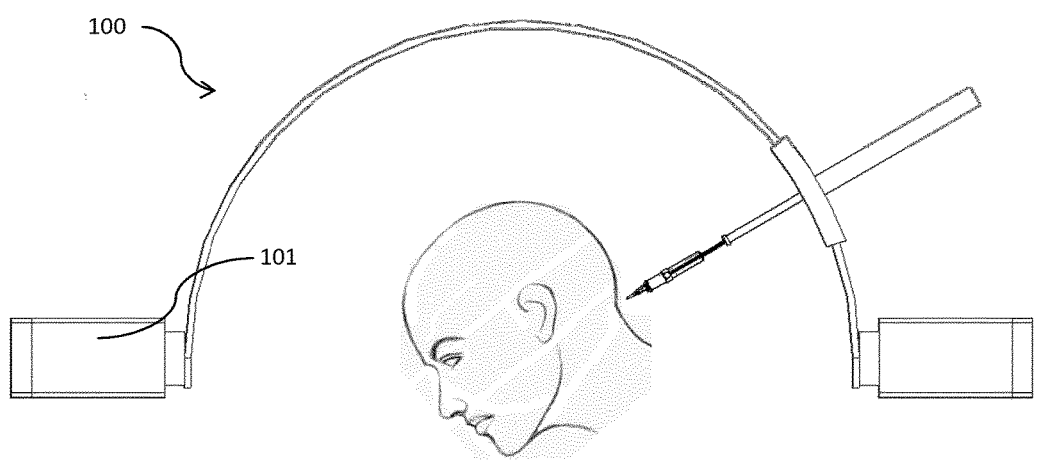
FIG. 2 demonstrates a side view of the harvesting position of the transplantation device according to the present invention.
Figure 3:
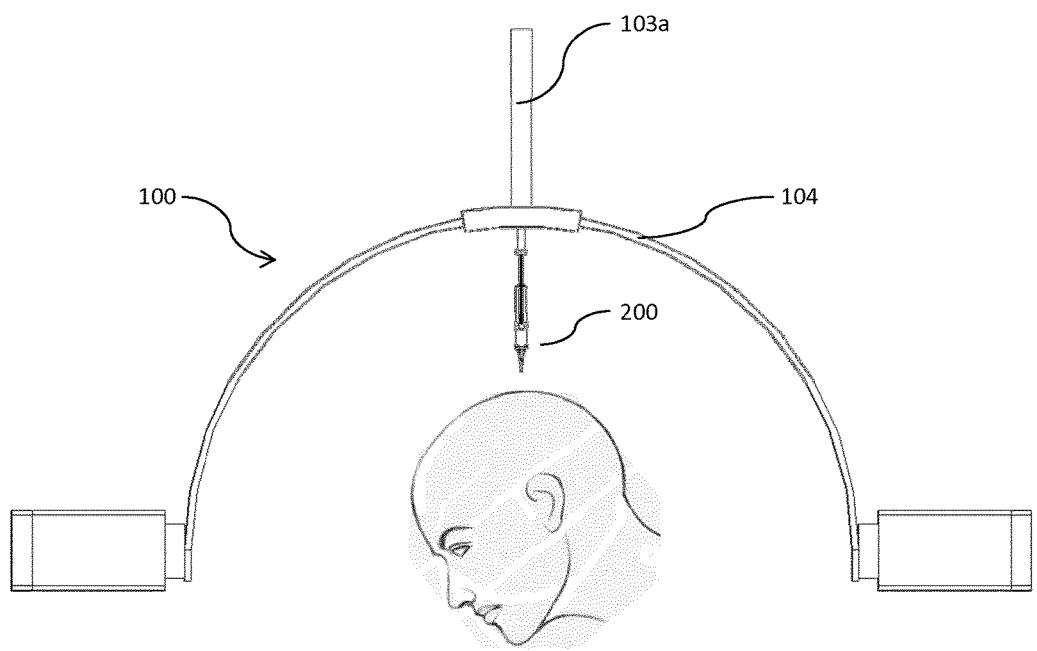
FIG. 3 demonstrates a side view of the transplantation device being motioned from harvesting process to the implanting process according to the present invention.
Figure 4:
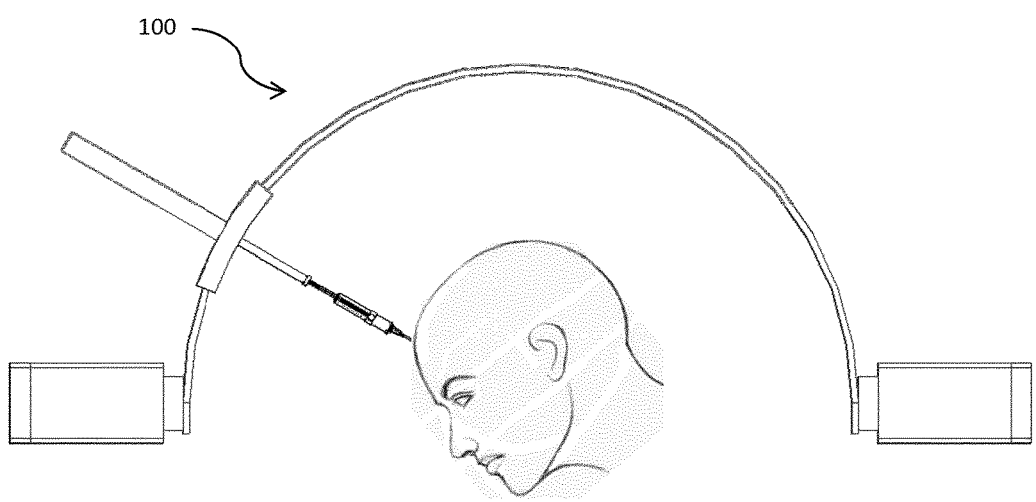
FIG. 4 demonstrates a side view of the transplantation device positioned for the implantation according to the present invention.

Referring now to the figures outlined above, the present invention proposes a follicular unit transplantation device. The following numerals are assigned to different parts demonstrated in the drawings:
100 Transplantation device
101 Motor
102 Slider motor
103a, 103b Linear motor:
104 Rail mechanism.
105a, 105b Tuning motor
106 Rail
107 Connection part
108a, 108b Connection bar
109 Horizontal bar
110 Fine-tuning member
111 Slider base
112 Gripper housing
113 Channel
114a, 114b Rotary motor
115 Gripper housing linear motor
200 Gripper
201 Main body
202 Tip portion
303 Safety member
203a, 203b Safety member inlet
204 Knife mechanism
205 Ejector
205a Ejector inlet
206 Inner mechanism
207 Gear member
208 Bearing
209, 211 Ring nut
210 Pinion gear
212 Bolt
213 Ring
214 Pinion spider
215 Guide member
216 Blade
217 Tubular body
218 Cutting, mechanism
219 Safety ring
220 Groove
221 Distal end
222 Knife
223, 224, 225, 226 Linear motor
227 Inner conic 230 Gear
231a, 231b Longitudinal tube
232 Coupling ring
233 Geared portion
234 Transmission member
235 Blade hole
236 Connection portion
237 Conduit
238 Knife slot
301a, 301b Upper camera and/or sensor
302 Lower camera and/or sensor
303 Fine tuning camera and/or sensor
400 Scalp
500 Follicular Unit
600a, 600b Gripper holding mechanism
"P" Point of gripper The present invention provides a follicular unit transplantation device (100) that is capable of perform precisely all phases of the follicular unit (500), especially hair follicular unit, transplantation such as harvesting and implanting, with a specifically designed gripper (200). Follicular unit transplantation generally includes three steps: follicular unit harvesting, recipient site incision and follicular unit implantation into the incision. All three of these main steps can be performed with the proposed transplantation device (100) which removes each hair follicle and transplant into the recipient site step by step.

A follicular unit transplantation device (100), shown in FIG. 1, mainly comprises a gripper (200) which is able to harvest, hold and implant the follicular unit (graft), a plurality of motor for the displacement of the gripper (200), a rail mechanism (104) formed at least partly in an arc-shaped form on which the gripper (200) slides by the motion of at least one slider motor (102) and at least one camera and one sensor (301a, 301b, 302, 303) placed around the device (100) for identifying follicular units (500) in a region of interest. Said transplantation device (100) harvests the follicular unit (500) and then implants step by step into the recipient site (e.g. balk area). The gripper (200) designed to perform the harvesting and the implanting processes of the transplantation automatically, completes the implanting process without leaving and holding the follicular unit (500) anywhere. In addition, harvested follicular unit (500) is never hold anywhere except inside of the said gripper (200) which is very important for hygiene and vitality of the follicular units.

Figure 10:
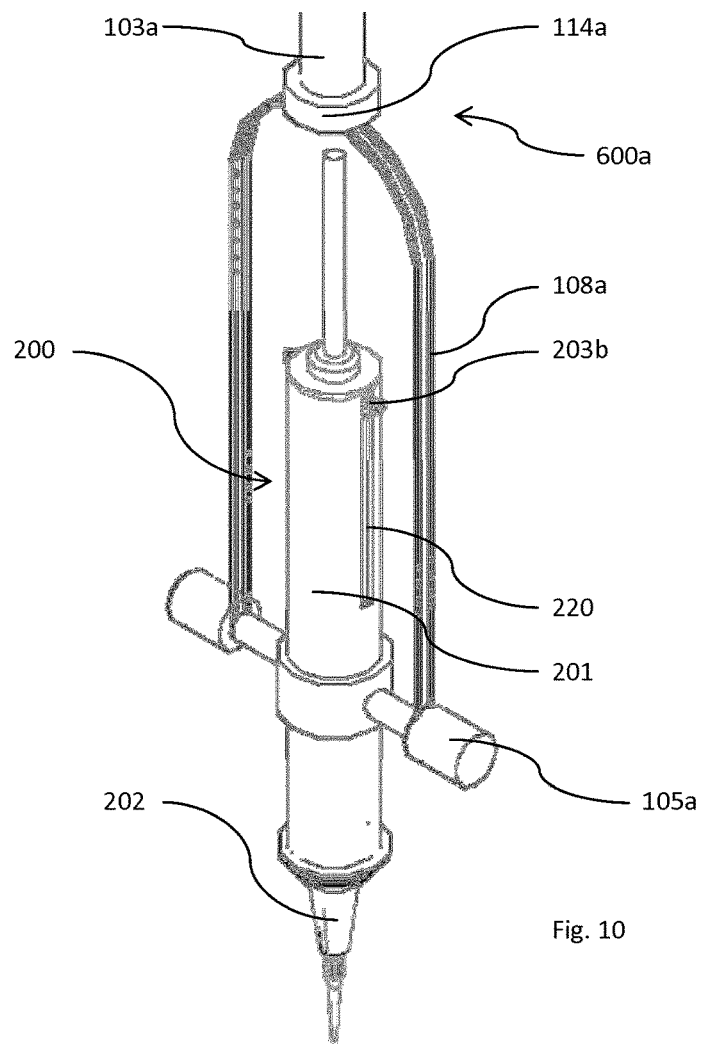
FIG. 10 demonstrates a perspective view of a gripper of the transplantation device according to the present invention.

As shown in FIG. 10, a gripper holding mechanism (600a) for holding and positioning the gripper (200) comprises a main body (201), a linear motor (103a) for exerting a force along the longitudinal axis of the gripper, a rotary motor (114a) for rotation of the gripper holding mechanism (600a) around its own axis, a connection bar (108a) in an U form to keep gripper (200) in a tight manner and at least one tuning motor (105a) for better alignment of the gripper (200). As will be appreciated by those skilled in the art, attachment of the gripper (200) to the rail mechanism (104) can vary.

Said gripper (200), as shown in FIG. 1, is attached to the rail mechanism (104) preferably having two rails (106) which is in an arc form, and slides through this rail mechanism (104). With this special design, the gripper (200) is capable of precisely moving on spherical, ellipsoidal or the like surfaces which is especially suitable for patient's head. Said rail mechanism (104) comprises at least one, preferably two rails (106) in an at least partly arc-shaped form. At the both end of the rail mechanism (104) are coupled with motor (101) for the positioning of the rail mechanism (104).

Figure 5:
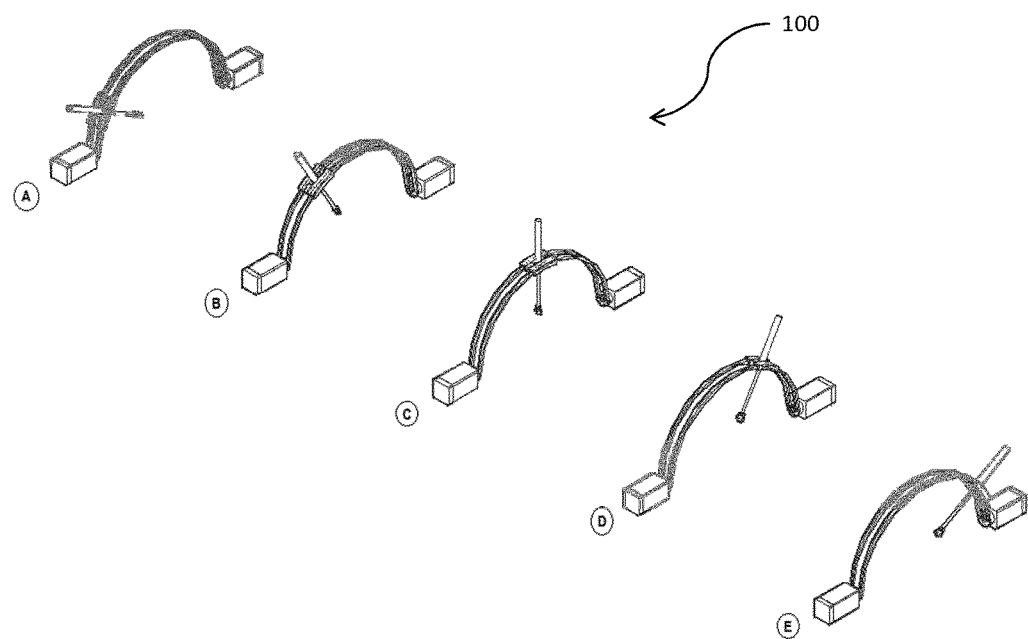
FIG. 5 demonstrates perspective views of displacement of the gripper on the rail of the transplantation device according to the present invention.
Figure 6:
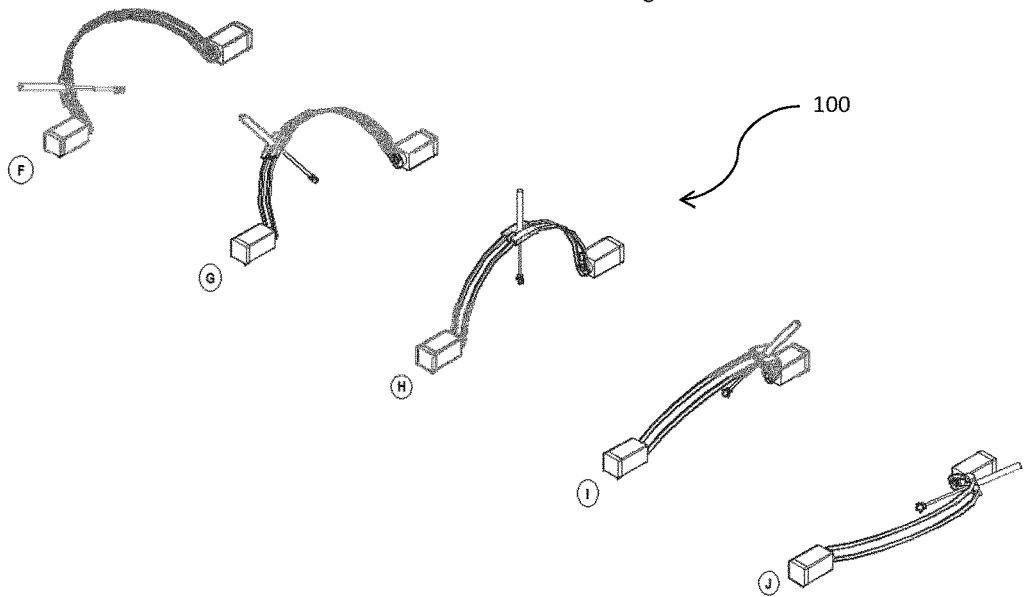
FIG. 6 demonstrates perspective views of displacement of the gripper and rail of the transplantation device according to the present invention.
Figure 7:
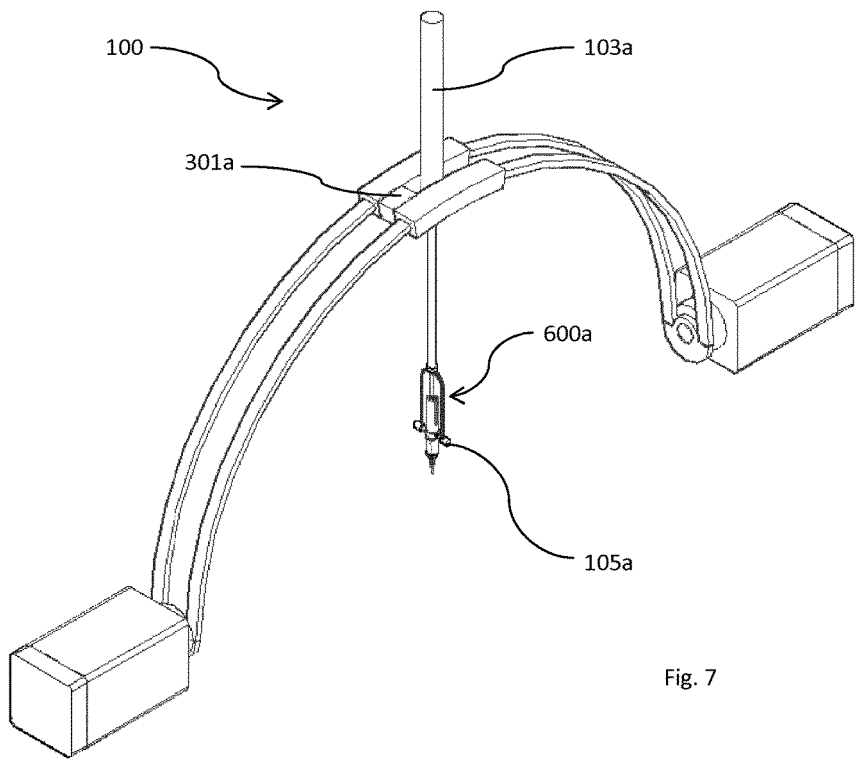
FIG. 7 demonstrates a perspective view of the transplantation device according to the present invention.
Figure 8:
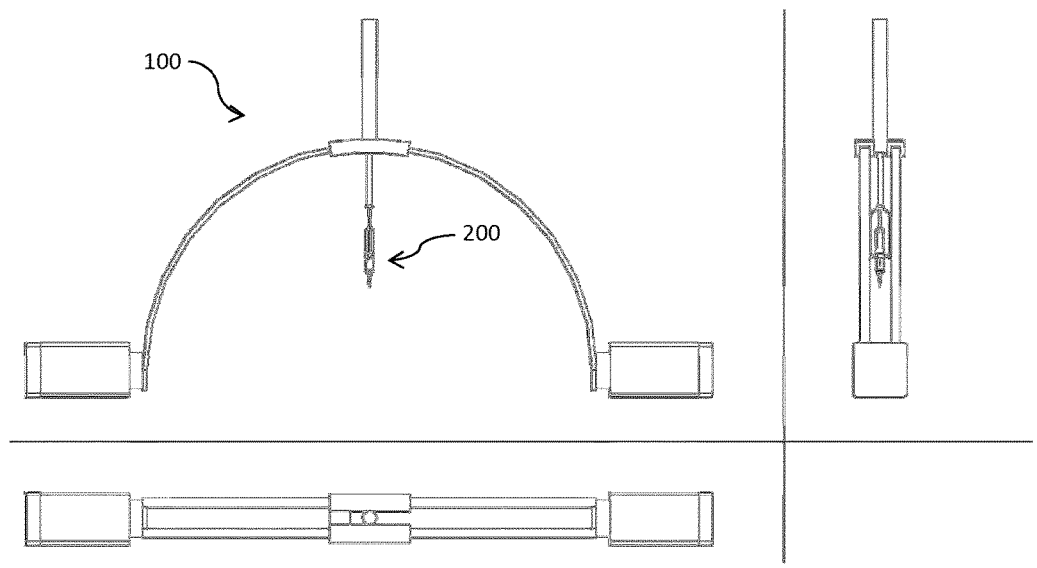
FIG. 8 demonstrates a side, front and an upper view of the transplantation device according to the present invention.
Figure 9:
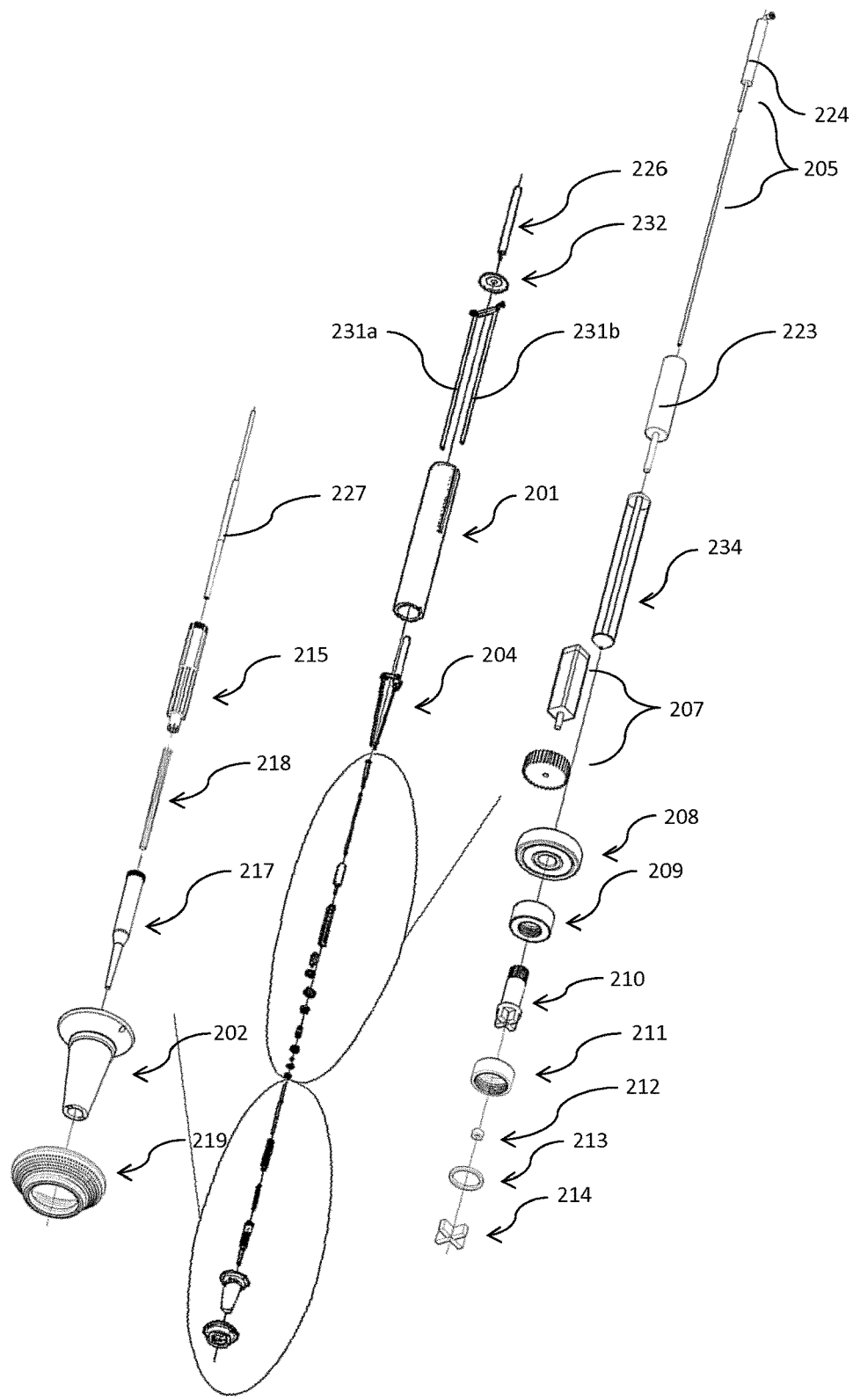
FIG. 9 demonstrates an exploded view of a gripper of the transplantation device according to the present invention.

The device (100) is generally coupled with a plurality of cameras and/or sensors, at the preferred embodiment; at least one upper camera and/or sensor (301a) are located between slider motors (102). In an alternative embodiment at least one lower camera and/or sensor (302) is placed between fine-tuning members (110). The horizontal, bar (109) passes through the lower cameras and/or sensors (302) and engages with the other connection bar (108b). In addition that, fine-tuning cameras and sensors (303), preferably, are placed surrounding of the gripper housing (112). Said camera(s) and/or sensor(s) (301a, 301b, 302, 303) are used for identifying follicular units (500) in a region of interest and then vision system computes the respective locations and orientations of the identified follicular units (500). Said camera(s) and/or sensor(s) (301a, 301b, 302, and 303) are, preferably, in a communication with computer and special software that is called vision system. Image data obtained by the upper and lower camera(s) and/or sensors) (301a, 301b, 302) is processed in a computer associated with the hair transplantation device (100). In alternate embodiments, only a single camera and/or sensor (301a, 301b, 302) can be used for image acquisition. In addition that, lights are also may be placed to the device (100). The vision system manages the motions of the gripper (200), the slider (102), the linear motor (103a, 103b) and rail mechanism (104) according to the SCS (spherical coordinate system). In addition, the vision system can perform a medical examination to the person to be applied hair implantation operation. At the end of this medical examination, the vision system reports the initial condition before the operation and the desired conditions after the operation. Said transplantation device (100) uses real-time information from the vision system to monitor the position of the patient and advance the gripper (200). Referring to FIG. 5 and FIG. 6, the gripper (200) of the device (100) is able to advance on almost every point of the recipient site on the scalp (400) by the rail system (104) manipulated according to the spherical coordinate system. The displacement of the gripper (200) is performed by using a plurality of motor that raise and lower the gripper (200) and slides the along the rail (104).

Prior to the operation, it is required to cut the hair follicles in the region(s) of interest to a substantially uniform length and the patient's recipient site (especially head) should be fixed according to the required position for the operation. In order to harvest a follicular unit (500) from a body surface (e.g., a scalp) the device (100) positions and aligns the gripper (200) with a longitudinal axis of a selected follicular unit to be harvested. Said desired position of the gripper (200) is positioned according to real-time image data information acquired from camera(s) an for sensor(s) (301, 302, 303). The fine tuning of the gripper (200) is adjusted via the vision system by using a plurality of motors which are, preferably, in a communication with at least one sensitive sensor. It is important that longitudinal axis of the follicular unit to be harvested and the zipper (200) are aligned on the same axis and direction.

Figure 12:
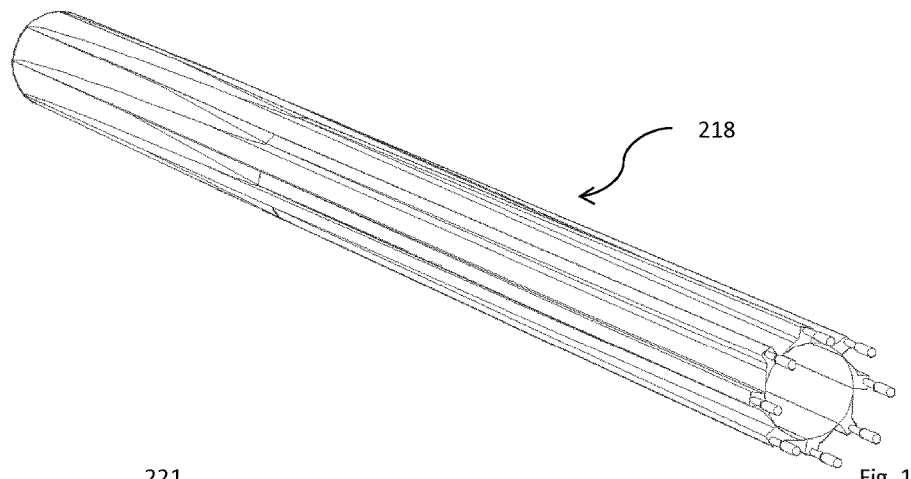
FIG. 12 demonstrates a perspective view of a cutting mechanism according to the present invention.
Figures 26, 27:
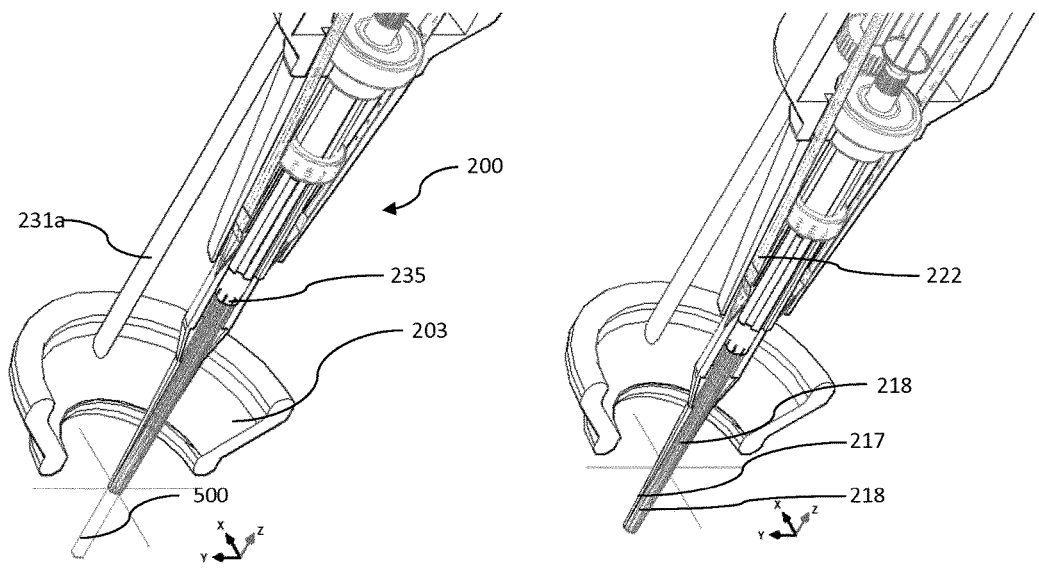
FIG. 26 demonstrates a partially cut-away sectional view of the transplantation device where the gripper is brought in a contact with the body surface according to the present invention.
FIG. 27 demonstrates a partially cut-away sectional view of the transplantation device where the punching process performs according to the present invention.

Referring to FIG. 26, after the alignment of the gripper (200) according to the longitudinal axis of the selected follicular unit (500), a safety member (203) comprising a safety ring (219) in a circular form having a plurality of holes, is lowered and brought in a contact with the recipient site (e.g., a scalp) via a linear motor (226) for patient protection. Said safety ring (219) attached with at least one longitudinal tube (231a, 231b) and a coupling ring (232) protects the scalp of the patient from unexpected damages which may occur by the gripper (200) during the operation. The safety ring (219) may also spray the solution fluid with air/gas on to the scalp in order to help to clean the harvested area. Said solution fluid with air/gas goes through the longitudinal tubes (231a, 231b) and reaches to the safety ring (219) for spraying to the body surface from a plurality of holes. The longitudinal tubes (231a, 231b) comprises safety member air inlet (2034) and safety member solution inlet (203b) which are guided by grooves (220) formed at the both side of the main body (201). A cutting mechanism (218), shown in FIG. 12, comprises a plurality of blades (216) having distal end (221) in a sharp configuration for allowing the penetration of tissue. Said blades (216) are coupled with at least one connection portion (236) at the upper portion for engagement with blade hole (235) of the guide member (215). Said guide member (215) is configured to rotate the blades (216) about its own vertical axis and moves the blades linearly to/from the central axis of the cutting mechanism (218). Said guide member (215) helps to keep the blades (216) together via blade hole (235) formed at lower portion sized and shaped to engage with the connection portion of the blades (216). In addition that, said guide member (215) rotates on its own axis with blades, meanwhile, said blades move away from central axis of the cutting mechanism. The numbers of the blade holes (235) of the guide member (215) are oriented according to the number of the blades (216).

Figure 11:
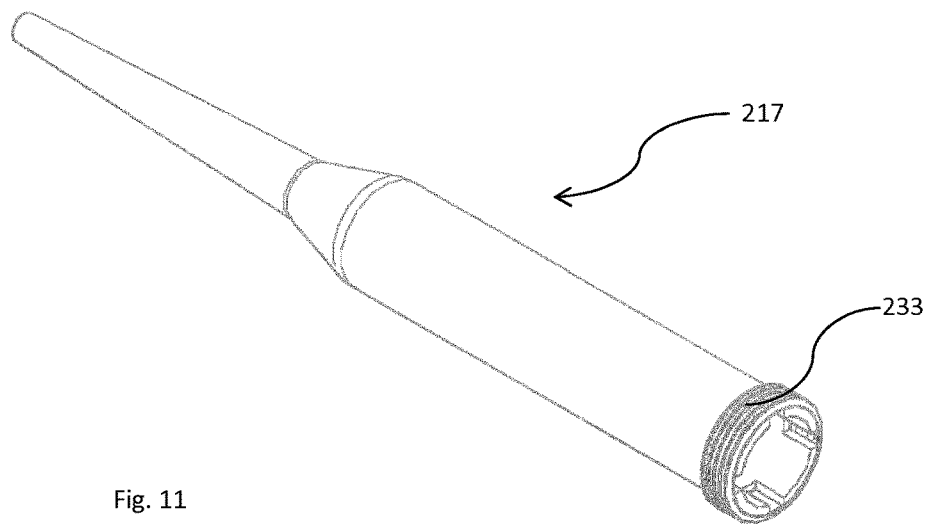
FIG. 11 demonstrates a perspective view of a tubular body of the transplantation device according to the present invention.
Figure 13:
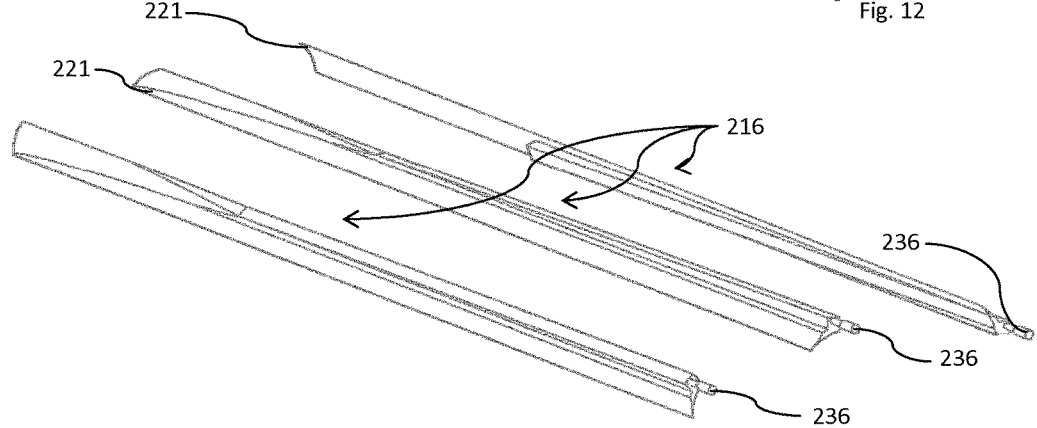
FIG. 13 demonstrates a perspective view of blades of a cutting mechanism according to the present invention.
Figure 14A:
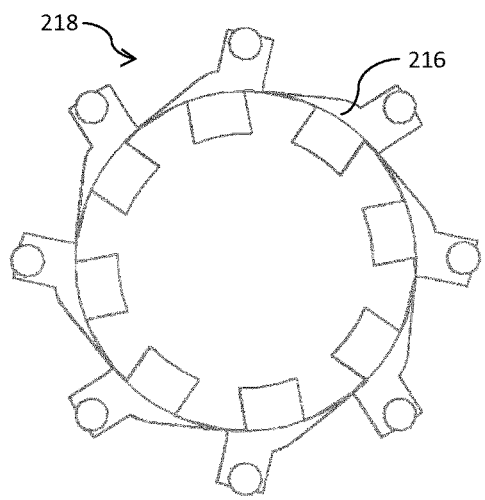
FIG. 14a demonstrates an upper view and opened position of a cutting mechanism according to the present invention.
Figure 14B:
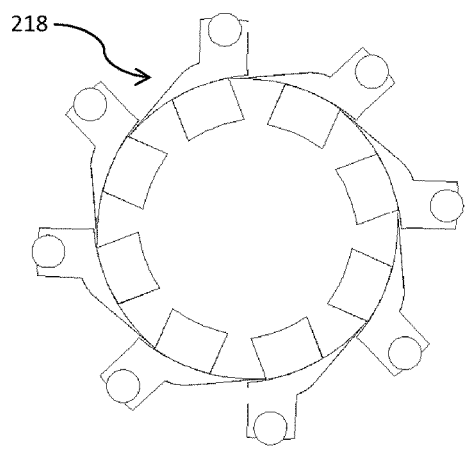
FIG. 14b demonstrates an upper view and closed position of a cutting mechanism according to the present invention.
Figure 15:
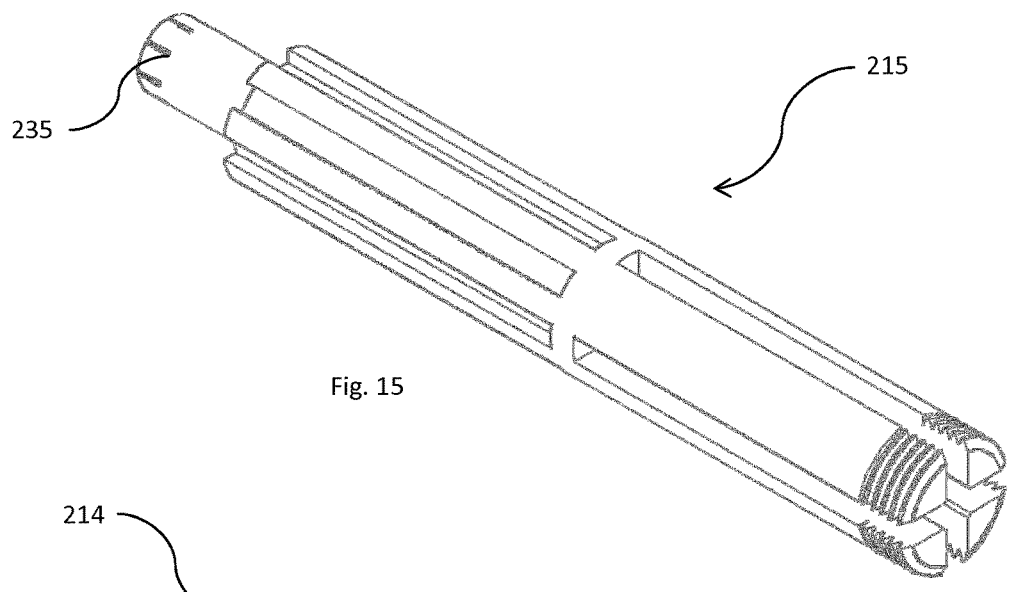
FIG. 15 demonstrates a perspective view of a guide member of the transplantation device according to the present invention.
Figure 16:
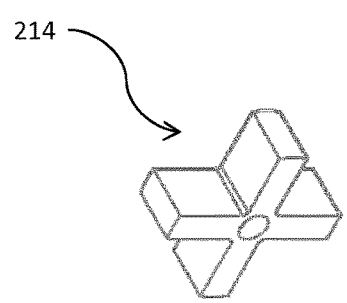
FIG. 16 demonstrates perspective views of the some pails of the gripper of the transplantation device according to the present invention.
Figure 16:
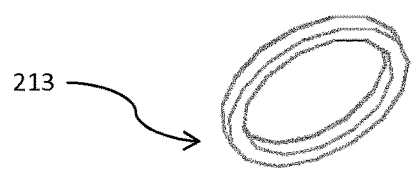
Figure 16:
Figure 16:
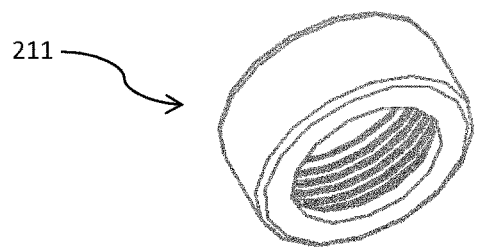

The cutting mechanism (218) always revolves around its own axis with tubular body (217) during the operation to harvest the outer periphery of the follicular unit (500) easier and increase the cutting performance. Combination of the blades (216) is in a lens aperture form as shown in FIG. 14a and FIG. 14b. In FIG. 26, the gripper (200) is advanced over the selected follicular unit (500) and touches to the donor area. As said gripper (200) touches the donor area e.g. scalp (400) punching process starts. THe tubular body (217) having geared upper portion (233) for transmission and narrowing lip portion, shown in FIG. 11, and a plurality of blades (216), shown in FIG. 13, start to penetrate the selected donor area by revolving on its own axis to a depth sufficient to substantially encapsulate the follicular unit. The cutting mechanism (218) is then retracted and removed from the patient. The pinion spider (214) matches with the inner area of the geared portion (233) of the tubular body (217) for the movement transmission.

Figures 28, 29:
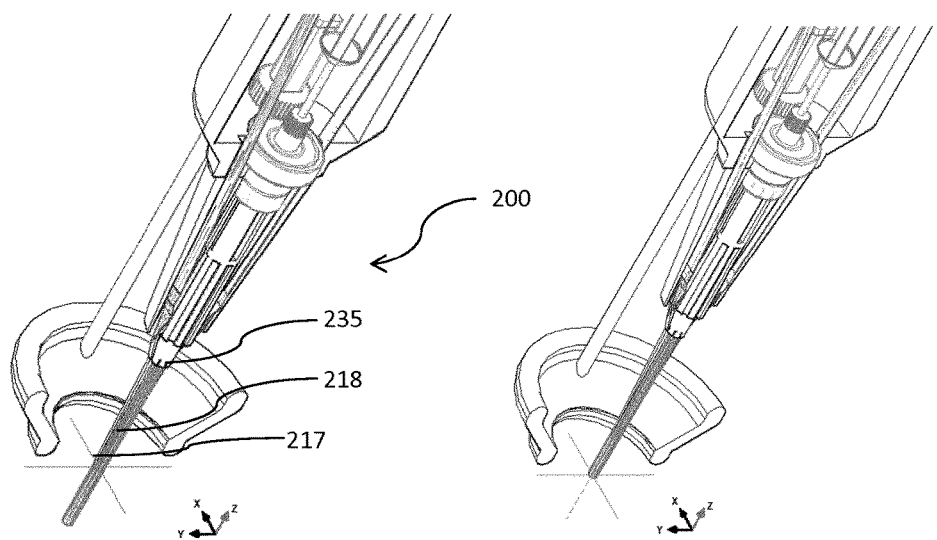
FIG. 28 demonstrates a partially cut-away sectional view of the transplantation device where the follicular unit is grasped by the cutting mechanism according to the present invention.
FIG. 29 demonstrates a partially cut-away sectional view of the transplantation device where the follicular unit is harvested and taken out from the body surface according to the present invention.

Said cutting mechanism (218) placed into the tubular body (217), formed with a plurality of blades (216), has an interior lumen appropriately sized for harvesting human follicular units (500). In order to calculate a depth of a selected object, such as a hair follicular unit, the images obtained from the camera(s) and/or sensor(s) (301, 302, 303) are used and the harvesting depth is determined by the vision system according to the follicular unit length. In FIG. 28, the follicular unit (500) harvesting process of the gripper (200) is illustrated. When the harvesting process is completed, the tubular body (21) and an inner conic (22) are lifted up with a transmission member (234) by way of linear motor (223). In FIG. 28, the cutting mechanism (218) keeps its position according to the longitudinal axis of the follicular unit (500) and then tubular body (217) moves up partially by sliding through cutting mechanism (218). While the tubular body (217) moves up by sliding on the exterior case of the cutting mechanism (218), said tubular body (217) squeezes blades (216) of the cutting mechanism (218). As the blades (216) are getting close to each other, the cutting mechanism (218) gasps tightly the follicular unit (500). The diameter of the cutting mechanism (218) is adjusted by the movement of the tubular body (217) on the blades (216) so that displacement of the tubular body (217) upwardly helps to hold tighter of follicular unit (500) which already encapsulated by the cutting mechanism (218). In The inner conic (227) which is simultaneously moved with the tubular body (217) on the same direction by way of linear motor (223), provides the stabilities of the blades (216) together with the tubular body (217). Next step, in FIG. 29, tightly grasped follicular unit (500) is then withdrawn by the gripper (200) then in FIG. 30; the gripper (200) is repositioned on the recipient site where the follicular unit (500) is to be implanted. Alternatively, an extraction mechanism, such as a vacuum, can be provided to extract or harvest the follicular unit (500).

Figures 30, 31:
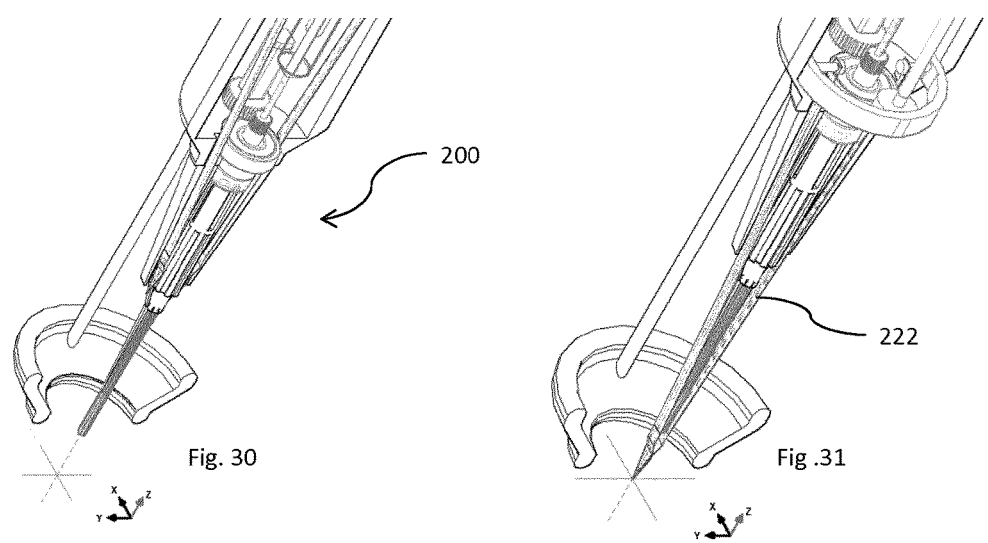
FIG. 30 demonstrates a partially cut-away sectional, view of the transplantation device where the transplantation device being located according to the present invention.
FIG. 31 demonstrates a partially cut-away sectional view of the transplantation device where the knife mechanism touches the recipient site for incision according to the present invention.
Figures 32, 33:
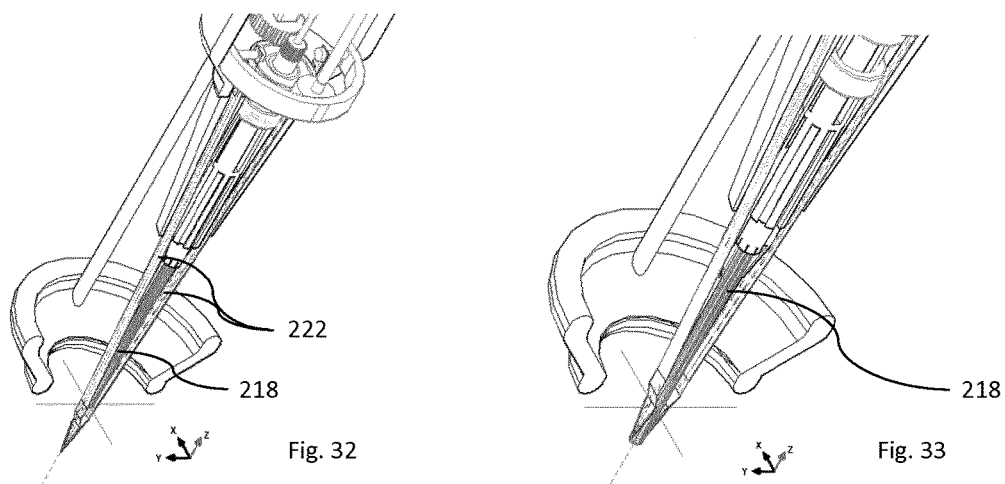
FIG. 32 demonstrates a partially cut-away sectional view of the transplantation device where the knife mechanism slides down for incision according to the present invention.
FIG. 33 demonstrates a partially cut-away sectional view of the transplantation device where the knife mechanism is withdrawn from the incision while the cutting mechanism is pushed into the incision according to the present invention.

At the implantation process, in FIG. 31, as the griper (200) is adjusted, at least one knife (222) of a knife mechanism (204) are pushed forward by via a linear motor (225) and the knives (222) having sharp distal end (221) and sharp point penetrates the tissue of the recipient site in order to open the required incision for the follicular unit (500) implanting process on the body surface. The distal end (221) of the blades (216) may be in arched and curved configuration for holding the follicular unit (500) tightly. In FIG. 32, as the incision opening process is completed, the cutting mechanism (218) holding follicular unit (500) inside, starts to slide down between the knives (222) by touching and flexing the knives (222). At the same time, the knives (222) are pulled up upwardly by the knife mechanism (204) while the cutting mechanism (218) is being downward pushed down. These two steps are simultaneously performed in order to leave the opened incision narrowly.

Notably, different sized tubular body (217) and blades (216) may be used for harvesting for harvesting follicular units. Also, it should be noted that the distal end (221) of the blades (216) can have different configurations in other embodiments, as long as it can penetrate tissue.

At the implantation process, the gripper (200) holding the follicular unit (500) inside, is ready to be located and positioned on the selected area and to be inserted into a recipient site in a same or different body Stir face or location from where the follicular unit (500) was harvested for implantation of the follicular unit (500). The gripper (200) is repositioned by the at least one motor to a selected implantation site on the body surface. At the implantation, a longitudinal axis of the follicular unit (500) (remains undisturbed since it was harvested) preferably aligned with a desired orientation.

FIG. 30 demonstrates a partially cut-away sectional view of the transplantation device according to the present invention. The gripper (200) automatically and precisely positions the cutting mechanism (218) and knife mechanism (204) at desired locations along a body surface (e.g., a scalp) of a patient based on control signals derived at least in part from image data obtained by at least one camera and/or sensor (301a, 301b, 302).

The knife mechanism (204), shown in FIG. 20, comprises at least two longitudinal knives (222) having arched, wavy sharp distal end. As the gripper (200) is advanced over to the selected point on the body surface, the knife mechanism (204) with sharp knives (222) lowers and touches the selected point in order to open incision on the recipient site. Referring to FIG. 32, incision opening on the recipient site is illustrated. As the knives (222) of the knife mechanism (204) touches to the selected point, the knives (222) moves down as much as follicular length and opens the incision into which the follicular unit (500) will be implanted. Next step, shown in FIG. 33, the knives (222) of the knife mechanism (204) reaches to the desired incision depth. The tubular body (217) and the blades (216) move down together into the incision by sliding between the knives (222). While the tubular body (217) and the blades (216) are lowered together, meanwhile, the knife mechanism (204) and knives (222) are raised from the incision. Aforementioned processes are performed simultaneously.

Figure 34:
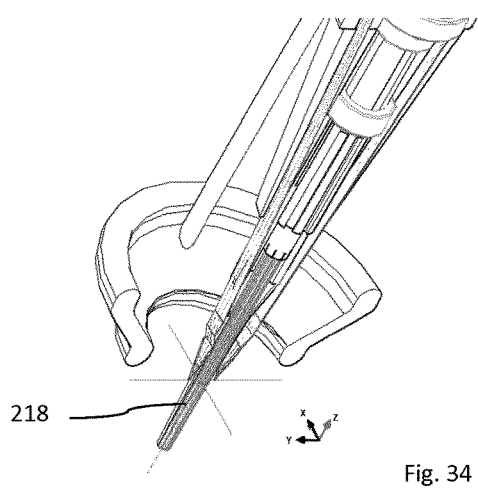
FIG. 34 demonstrates a partially cut-away sectional view of the transplantation device where the blades arrive to the bottom of the incision and the knife mechanism completely leaves the incision according to the present invention.
Figure 35:
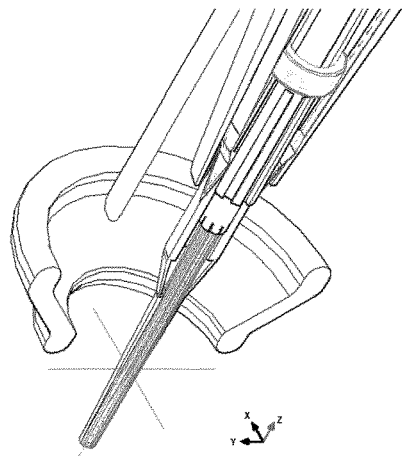
FIG. 35 demonstrates a partially cm-away sectional view of the transplantation device where loosening process of the harvested follicular unit is performed according to the present invention.

FIG. 34 demonstrates a partially cut-away sectional view of the hair transplantation device where the blades (216) arrive to the bottom of the incision according to the present invention. The tubular body (217) and the blades (216) move down and blades (216) arrive to the bottom of the incision, meanwhile, the knife mechanism (204) leave the incision completely. As the blade (216) of the cutting mechanism (218) arrives to desired length of the incision, the tubular body (217) starts to move down by sliding on the blades (216). Movement towards to the recipient site of the tubular body (217) causes loosens of the firmly tight follicular unit (500). As shown in FIG. 35, when the tubular body (217) reaches to desired length of the incision, the follicular unit (500) is completely loosened by the blades (216) of the cutting mechanism (218). At the end of this step, the follicular unit (500) is ready to be ejected from the gripper (200). As mentioned before conical exterior shape of the blades is used for tightening or loosening the kept follicular unit (500).

Figure 23:
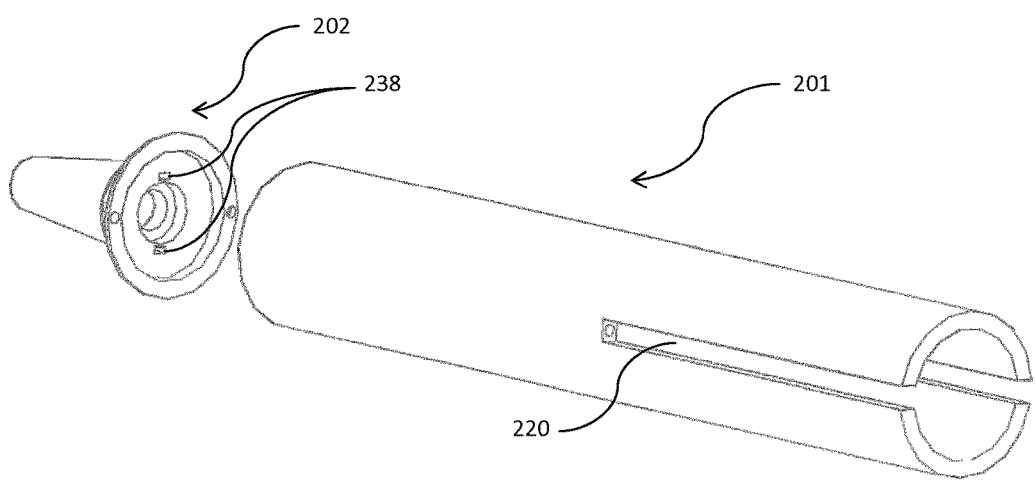
FIG. 23 demonstrates a perspective view of a tip portion and a main body of the transplantation device according to the present invention.
Figures 24, 25:
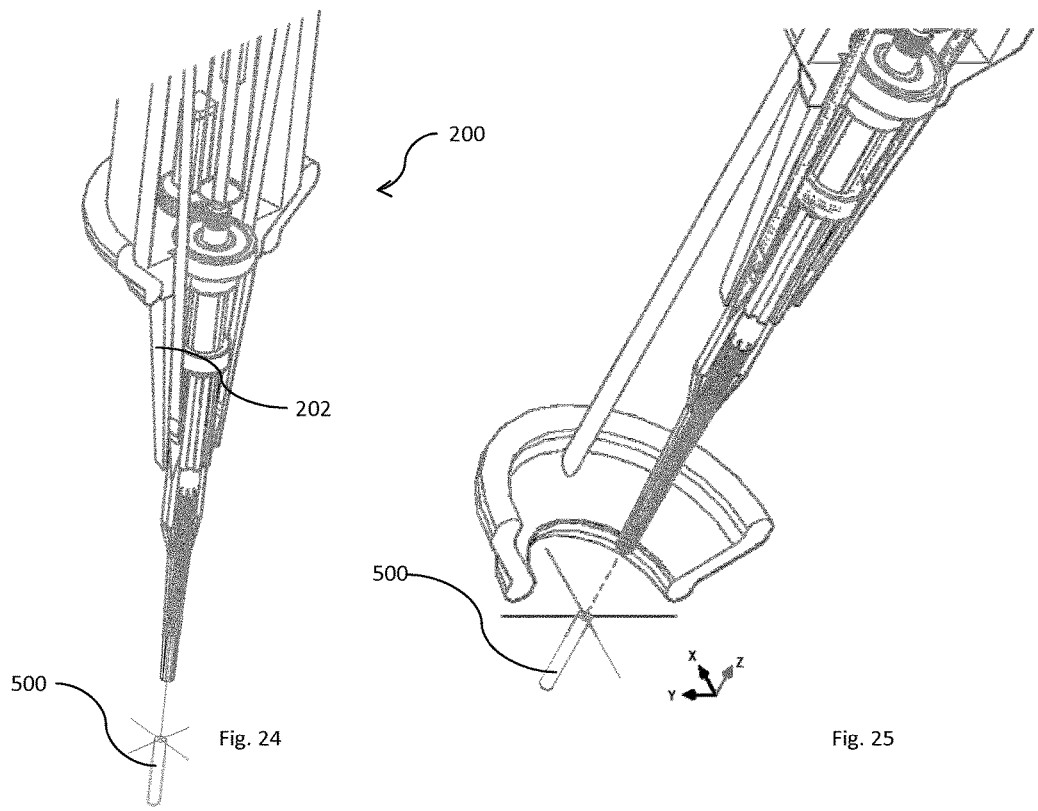
FIG. 24 demonstrates a partially cut-away sectional view of the transplantation device where the device is in stand-by mode according to the present invention.
FIG. 25 demonstrates a partially cut-away sectional view of the transplantation device where the safety member is brought in a contact with the body surface according to the present invention.

As shown in FIG. 23, a tip portion (202) is attached to the main body (201) and through which the tubular body (217) passes. Said tip portion (202) comprises at least one life slot (238) through the knives (222) is directed to incision for opening.

Figures 17, 18:
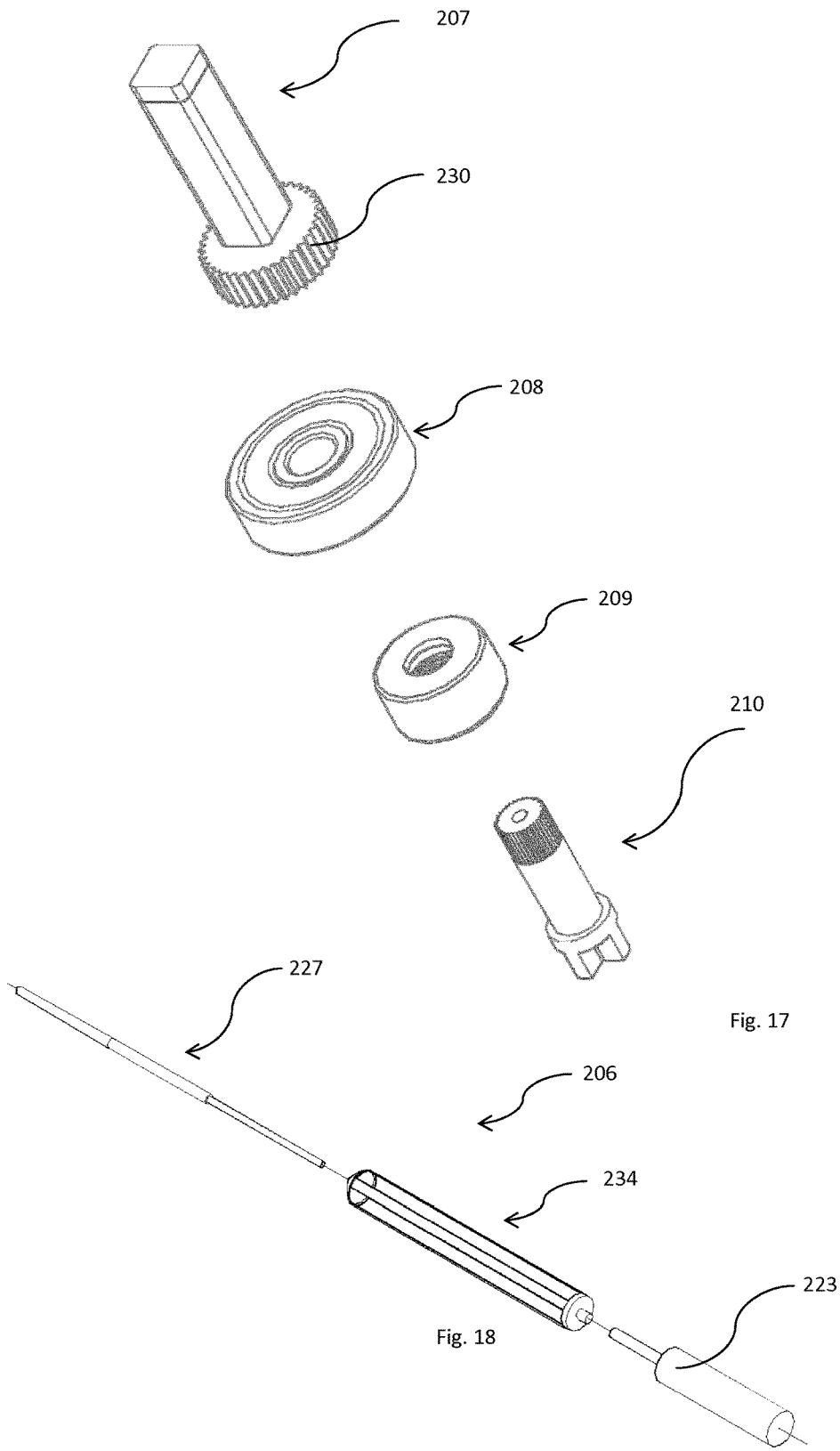
FIG. 17 demonstrates perspective views of the some parts of the gripper of the transplantation device according to the present invention.
FIG. 18 demonstrates a perspective view of an inner body of the transplantation device according to the present invention.
Figure 22:
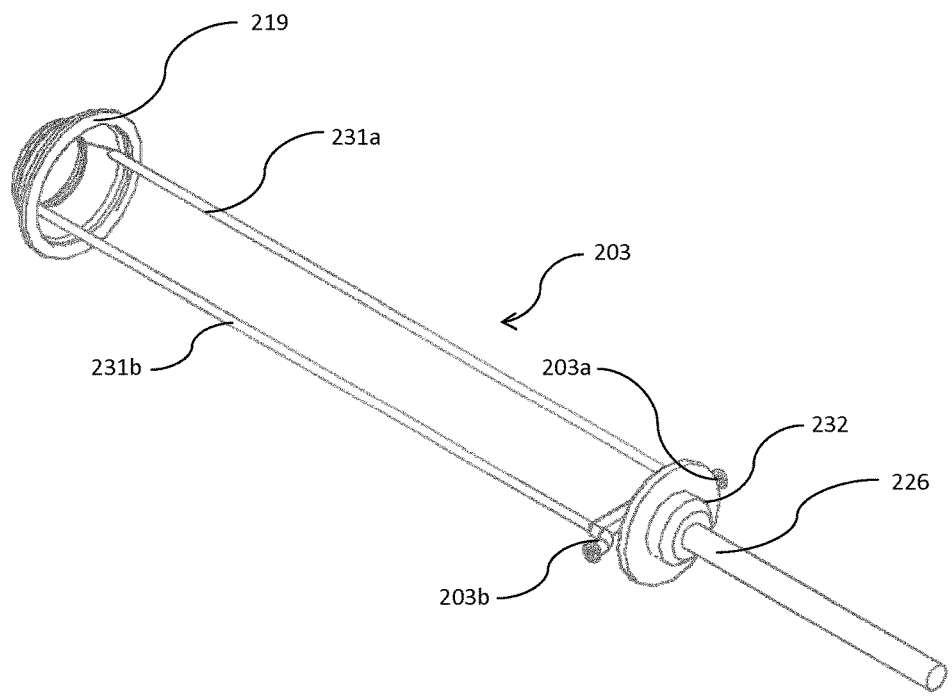
FIG. 22 demonstrates a perspective view of a safety member of the transplantation device according to the present invention.

In the illustrated embodiments, the gripper (200) comprises a plurality of resilient members that are attached to or integral with said gripper. A gear member (207 coupled with a gear (230) shown in FIG. 17, drives a pinion gear (210) and guide member (215) as well. A bearing (208) is used to helps the rotation of the pinion gear (210). A ring nut (209) is used for the coupling of the pinion gear (210) and guide member (215). Displacement of the guide member (215) drives the tubular body (217) and cutting mechanism (218). Said guide member (215) ensures linear motion of the tubular body (217) and slide. A pinion spider (214), the ring (213) and the ring nut are used for the coupling and force transitions between the guide member (215) and tubular body (217). A ring nut (211) matches with the geared upper portion of the guide member (215). The guide member (215) keeps blades (216) together and helps their linear and rotational motions. A bolt (2121 is used for the coupling and force transitions between the inner mechanism (206) and tubular body (217) via the pinion spider (214). The inner conic (227) and the tubular body (217) are moved linearly and simultaneously by the inner mechanism (206) via a linear motor (223).

Figure 36:
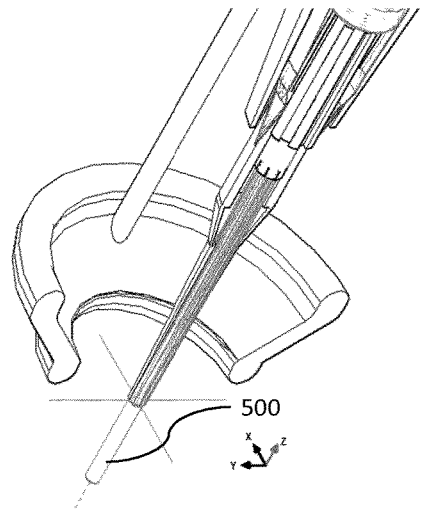
FIG. 36 demonstrates a partially cut-away sectional view of the transplantation device where the ejecting and leaving process of the follicular unit is performed according to the present invention.

In FIG. 36, the process of the ejecting and leaving the follicular unit (500) is illustrated. The follicular unit (500) is loosened completely by the displacement of the tabular body (217). The tubular body (217) and the blades (216) start to move up together from the recipient site and leave the follicular unit (500) into the incision on the recipient site. At the same time, an ejector (205) starts to move down via a linear motor (224) through an inner mechanism (206) to make easier the follicular unit (500) to be implanted completely into the incision by pushing. Said ejector (205) which is placed inside of the guide member (215) moves along the way of the guide member (215).

Figure 37:
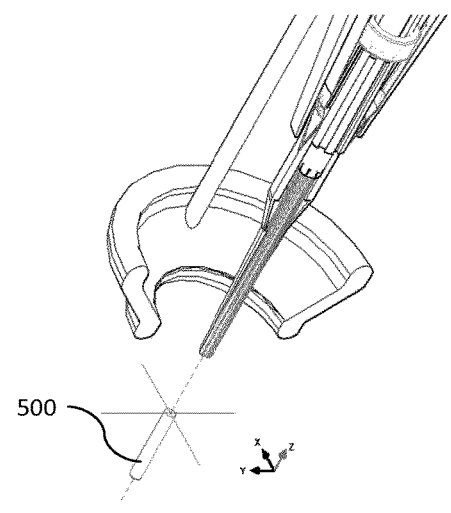
FIG. 37 demonstrates a partially cut-away sectional view of the transplantation device where the transplantation device prepared for the next harvesting operation according to the present invention.

By the completion of the follicular unit (500) ejecting process, the recipient site starts to squeeze the newly implanted follicular unit (500). During the whole process, the ejector (205) comprising a conduit (237) and an ejector inlet (205a) suitable for receiving cleaning solution that may spray the liquid solution and/or air to clean inside of the cutting mechanism (218) and tubular body (217) In FIG. 37, the preparation for the next harvesting operation, is illustrated. The gripper (200) moves away from the recipient site and advances to harvesting area for the next hair follicular unit. The dipper (200) takes its position and starts the next harvesting process as soon as the gripper (200) is located on the harvesting area. All these processes are repeated again and again until the last follicular unit (500) is implanted into the recipient site. A plurality of motor may comprises control circuitry for controlling operation of the respective motors. The control circuitry may include an independent processor (not shown) associated with the motors, which receives a data inputs from the visual system, including but not limited to positioning data obtained from images.

Figure 38:
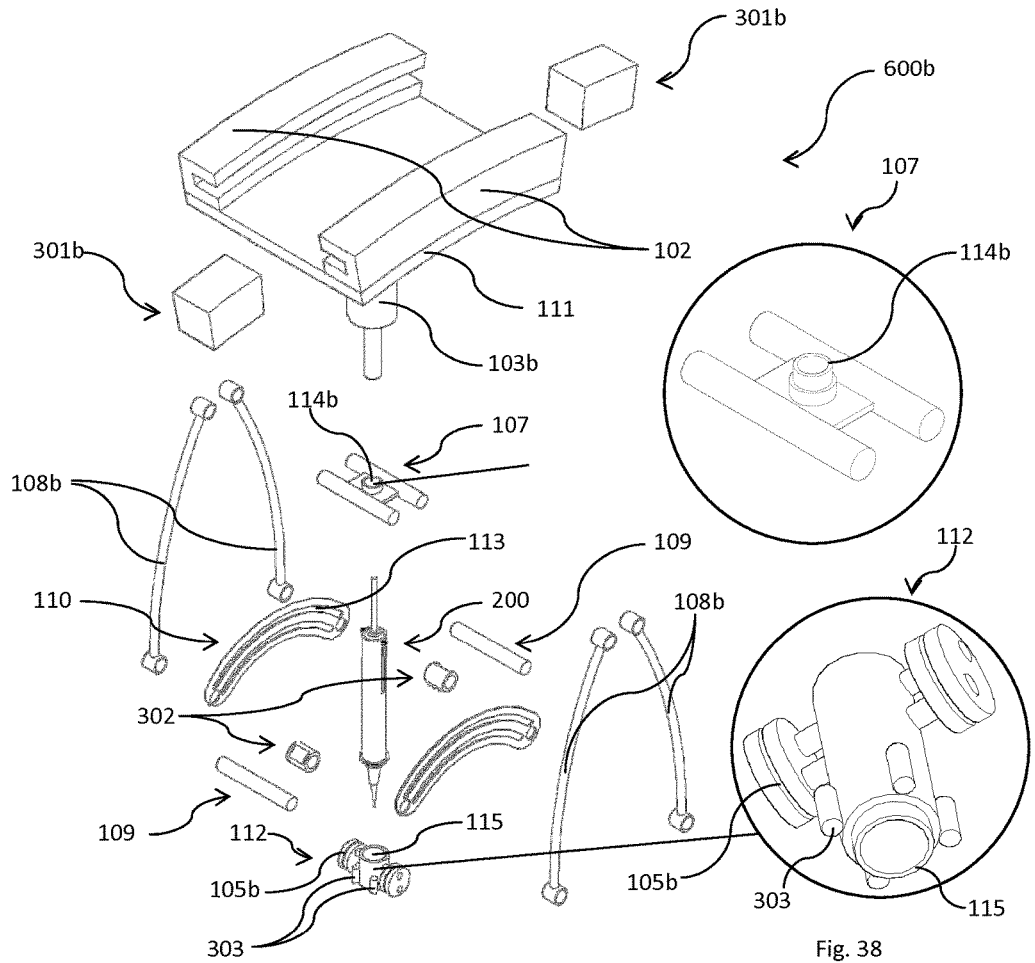
FIG. 38 demonstrates an exploded view of a gripper holding mechanism according to the present invention.
Figure 39:
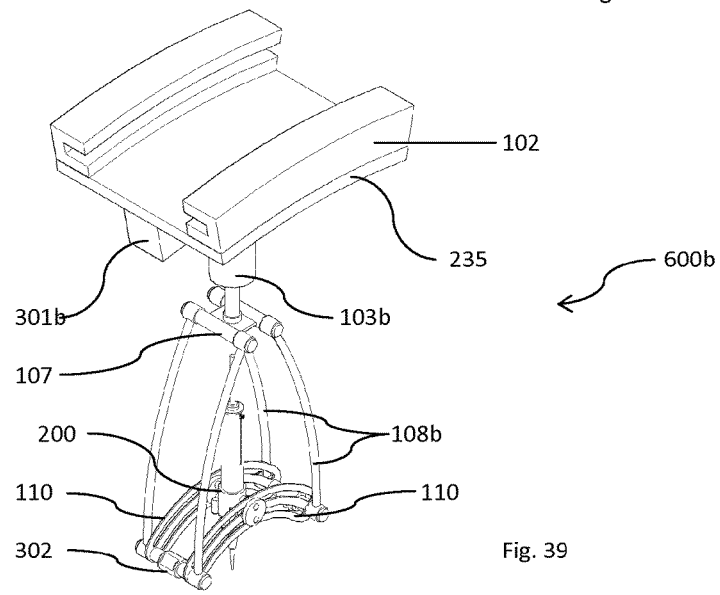
FIG. 39 demonstrates a perspective view of a gripper holding mechanism according to the present invention.
Figure 40A:
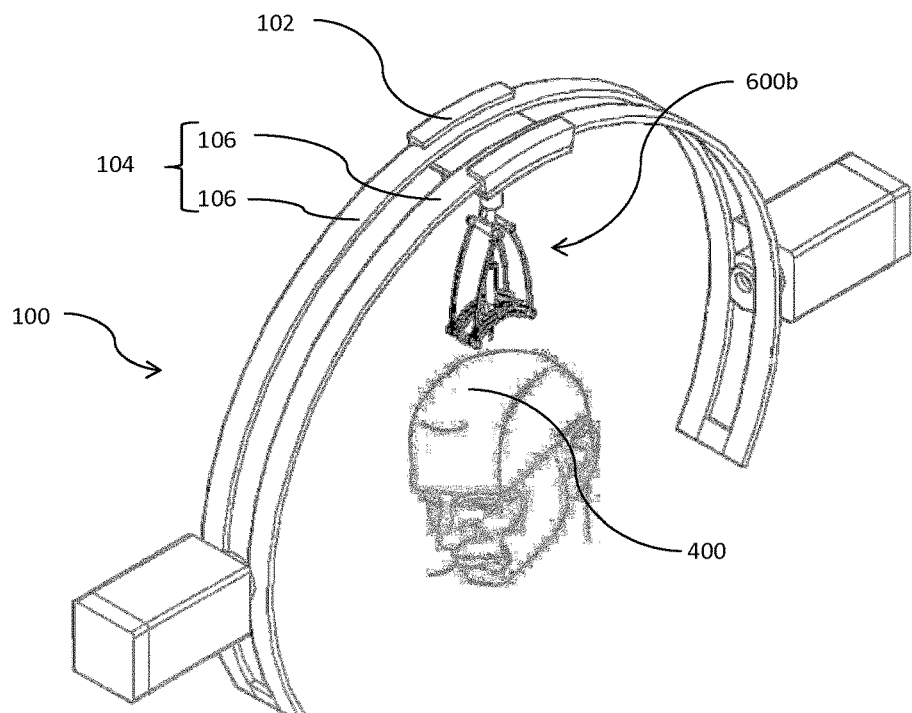
FIG. 40a demonstrates a perspective view of a transplantation device where an alternated gripper holding mechanism is attached to the rails according to the present invention.
Figure 40B:
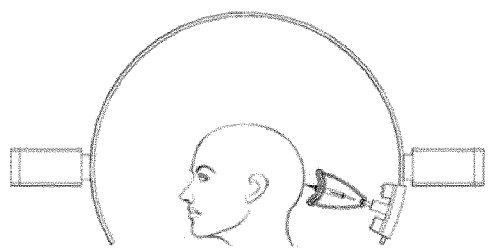
FIG. 40b demonstrates a side view of the harvesting position of the transplantation device according to the present invention.
Figure 40C:
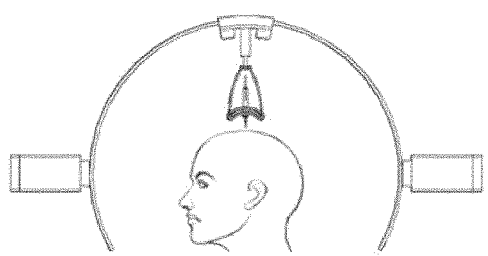
FIG. 40c demonstrates a side view of the transplantation device being motioned from harvesting process to the implanting process according to the present invention.
Figure 40D:
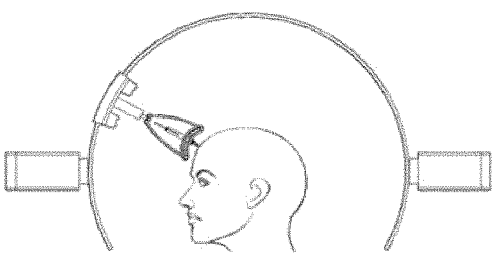
FIG. 40d demonstrates a side view of the transplantation device positioned for the implantation according to the present invention.

One alternate embodiment for attachment of the gripper (200) is shown in FIGS. 38 and 39. In FIG. 39, said gripper (200) is hold by an alternative gripper holding mechanism (600b) then attached to the rail mechanism (104). As shown in FIG. 43a, 43b, θ, Φ are used for directing gripper (200) to a particular target. The gripper holding mechanism (600b) comprises slider motor (102) with a slider base (111) for positioning on the rail mechanism (104), at least one upper camera and/or sensor (301b) placed around said slider ba se (111), a linear motor (103b) for horizontal positioning ("r" parameter as shown in FIG. 43b) of the gripper, a connection part (107) coupled with a rotary motor (114b) attached to the linear motor (103a) which is suitable for the attachment of at least one connection bar (108b) at least one fine-tuning member (110) in an at least partly arc-shaped form and comprising at least one channel on which a gripper housing (112) attached, at least one horizontal bar (109) for engagement of the at least one fine tuning member (110). Said gripper (200) is kept by the gripper housing (112) and said housing (112) is attached to the channels (113) of the fine-tuning member (110) as shown in FIG. 39. Said gripper housing (112) comprising a tuning motor (1056) for better alignment is surrounded by fine tuning cameras and/or sensors (303) for determining a relative position and orientation of the gripper according to the follicular unit (500). Said gripper housing (112) comprising a gripper housing linear motor (115) to drive the gripper forward/backward on the direction of the vertical axis of the gripper (200). Position and the numbers of the cameras and or sensors (301, 302, 303) may vary. A computer is then may use to correlate the position of the targeted scan image in the scanned image coordinate system with the corresponding parameters r, θ, Φ, α, d (shown in FIG. 41b and in FIG. 43b) to enable the user to apply the gripper (200) to the targeted area of the donor or recipient area.

By the help of this spherical coordinate system, the gripper (200) is able to be positioned easier than the complex robotic systems. This simple and effective designed rail mechanism (104) designed according to the SCS (spherical coordinate system) performs to position the gripper (200) to the desired point in a very short time comparing to the complex robotic transplantation devices. As shown in FIGS. 43a and 43b, O; defines origin, P defines point of gripper, r: radius, (distance from "P" to "O"), Φ defines an angle between Z-axis and the longitudinal axis of the gripper, θ defines an angle between OQ line and X-axis. Time rail mechanism (104), linear motor (103a, 103b), motor (101) and slider motor (102) designed according to the spherical coordinate system are used to position the point of gripper P (r, Φ, θ). displacement of the gripper (200) according to the "T", shown in FIG. 43a, is arranged by the linear motor (103b), displacement of the gripper according to the "Φ" is arranged by slider motor (102) and θ is arranged by the motor (101).

Figure 41A:
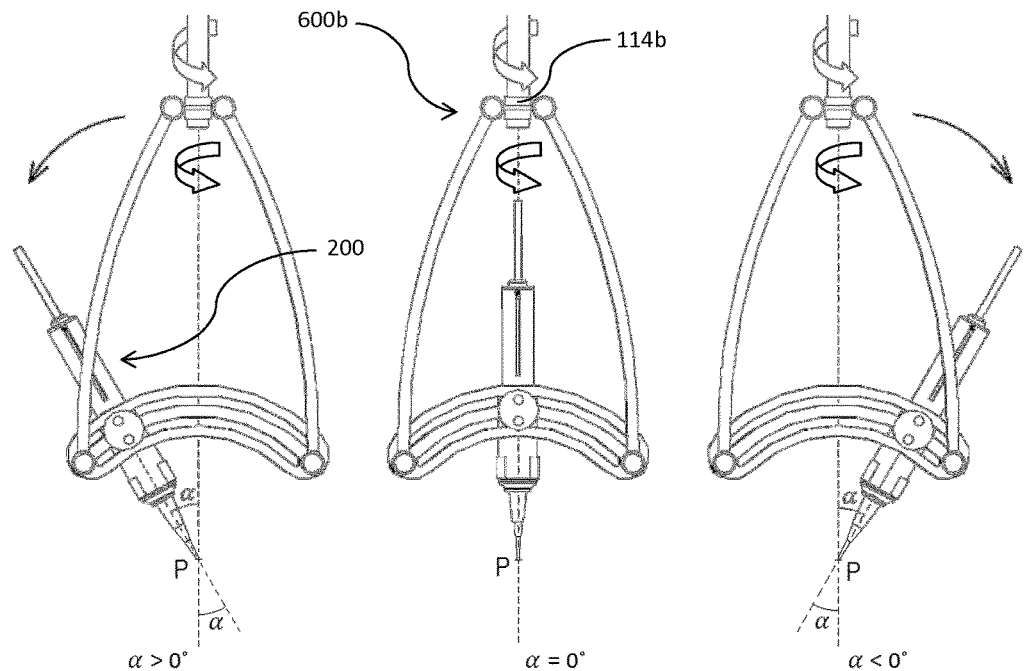
FIG. 41a demonstrates side views of the different displacements of the gripper of a holding mechanism according to the present invention.
Figure 41B:
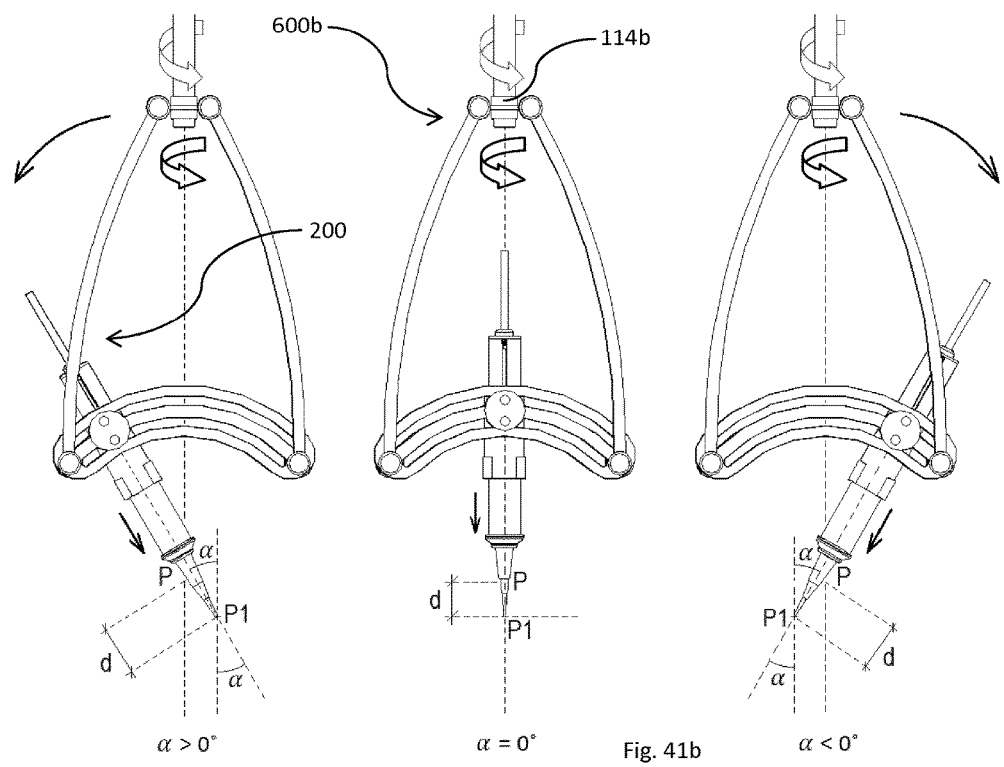
FIG. 41b demonstrates side views of the linear displacements on its longitudinal axis of the gripper holded by the holding mechanism according to the present invention.

The point ("P") of the gripper (200) located by the device (100) is positioned according to "r, Φ, θ" parameters. As shown in FIG. 41a, firstly the "P" is located on to the harvested follicular unit (500), and then the direction of longitudinal axis of the gripper (200) is finely tuned by the tuning motor (105b) according to the longitudinal axis of the follicular unit (500) The illustrated u angel which is between "P" and longitudinal axis of the linear motor (103b) is adjusted by the tuning motor (105b). Next step, the gripper point ("P") is kept stable and actuated by the tuning motor (105b) through the fine-tuning member (110) during the fine-tuning period of the gripper (200). After the alignment of the longitudinal axis direction of the gripper (500), said gripper (200) is linearly actuated forward to the point of "P1" by the gripper housing linear motor (115). In FIG. 41b, the distance between the "P-P1" is shown as "d" parameter. The value of the "d" parameter is determined according to the length of the follicular units (500) which will be harvested. The "d" parameter is preferably equal to the length of the follicular units (500) and depth of the harvesting process.

It should be noted that said gripper (200) or gripper holder mechanisms (600a and 600b) may be attached to the different type of robotic systems.

It is to be noted that said device (100) comprises a combination of motors, cams, and arcs, but any suitable mechanism can be used to provide translational and rotational movement of the gripper parts and rail mechanism.

The invention claimed is:

1. A transplantation device for a transplantation of a follicular unit, comprising: a gripper for harvesting and implanting the follicular unit, a rail mechanism comprising at least one rail for positioning the gripper at a predetermined orientation with respect to a donor or a recipient area, a gripper holding mechanism for holding the gripper attached to the rail mechanism wherein the gripper slides along the at least one rail, at least one camera and/or sensor for image acquisition to identify and determine a relative position and orientation of the gripper, a plurality of motors for positioning of the gripper and the rail mechanism, wherein the gripper further comprises a cutting mechanism formed of a plurality of blades for penetrating an outer periphery of the follicular unit on the donor area, a knife mechanism for opening an incision on the recipient area, a tubular body moving along a circumference of the cutting mechanism to hold tightly or loose the follicular unit, an ejector for pushing the follicular unit into the incision.

2. The transplantation device according to claim 1, wherein the rail mechanism is formed in at least partly arc-shape.

3. The transplantation device according to claim 1, wherein the gripper holding mechanism comprises at least one fine-tuning member with at least one channel for aligning the relative position of the gripper.

4. The transplantation device according to claim 1, wherein the gripper holding mechanism further comprises a gripper housing linear motor to move the gripper, when in use, according to a longitudinal axis of the gripper.

5. The transplantation device according to claim 1, further comprising at least one slider motor for positioning the gripper holding mechanism along the at least one rail.

6. The transplantation device according to claim 1, wherein the gripper further comprises a safety member having a safety ring with a plurality of holes through which a fluid passes.

7. The transplantation device according to claim 6, wherein the safety member comprises at least one longitudinal tube which are coupled with the safety ring.

8. The transplantation device according to claim 1, wherein the gripper further comprises a guide member having a plurality of blade holes for keeping the plurality of blades together.

9. The transplantation device according to claim 1, wherein the ejector comprises a conduit suitable for receiving and sending a fluid.

10. The transplantation device according to claim 1, wherein the cutting mechanism is in a lens aperture form.

11. The transplantation device according to claim 1, wherein the plurality of blades comprises distal ends in a wavy and sharp configuration for penetrating a tissue.

* * * * *